US012370258B2

(12) United States Patent
Gutierrez et al.

(10) Patent No.: US 12,370,258 B2
(45) Date of Patent: Jul. 29, 2025

(54) PD-1 AND CTLA-4 DUAL INHIBITOR PEPTIDES

(71) Applicant: Leidos, Inc., Reston, VA (US)

(72) Inventors: Gabriel M. Gutierrez, Reston, VA (US); Vinayaka Kotraiah, Reston, VA (US); Timothy W. Phares, Reston, VA (US); James Pannucci, Reston, VA (US)

(73) Assignee: Leidos, Inc., Reston, VA (US)

( * ) Notice: Subject to any disclaimer, the term of this patent is extended or adjusted under 35 U.S.C. 154(b) by 596 days.

(21) Appl. No.: 17/317,985

(22) Filed: May 12, 2021

(65) Prior Publication Data

US 2021/0275669 A1 Sep. 9, 2021

Related U.S. Application Data

(62) Division of application No. 15/989,750, filed on May 25, 2018, now Pat. No. 11,033,622.

(60) Provisional application No. 62/510,900, filed on May 25, 2017.

(51) Int. Cl.

| | |
|---|---|
| ***A61K 39/395*** | (2006.01) |
| ***A61K 31/7105*** | (2006.01) |
| ***A61K 35/17*** | (2025.01) |
| ***A61K 35/76*** | (2015.01) |
| ***A61K 38/00*** | (2006.01) |
| ***A61K 39/00*** | (2006.01) |
| ***A61K 39/39*** | (2006.01) |
| ***A61K 45/06*** | (2006.01) |
| ***A61P 31/04*** | (2006.01) |
| ***A61P 33/06*** | (2006.01) |
| ***A61P 35/00*** | (2006.01) |
| ***C07K 7/06*** | (2006.01) |
| ***C07K 7/08*** | (2006.01) |
| ***C07K 14/705*** | (2006.01) |
| ***C07K 16/28*** | (2006.01) |
| ***C12N 15/00*** | (2006.01) |

(52) U.S. Cl.

CPC .... *A61K 39/39558* (2013.01); *A61K 31/7105* (2013.01); *A61K 35/17* (2013.01); *A61K 39/0011* (2013.01); *A61K 39/39* (2013.01); *A61K 45/06* (2013.01); *A61P 35/00* (2018.01); *C07K 7/06* (2013.01); *C07K 7/08* (2013.01); *C07K 14/70521* (2013.01); *C07K 14/70532* (2013.01); *C07K 16/2818* (2013.01); *C07K 16/2827* (2013.01); *C12N 15/00* (2013.01); *A61K 35/76* (2013.01); *A61K 38/00* (2013.01); *A61K 2039/505* (2013.01); *A61P 31/04* (2018.01); *A61P 33/06* (2018.01)

(58) Field of Classification Search

CPC .......... A61K 39/39558; A61K 31/7105; A61K 35/17; A61K 39/0011; A61K 39/39; A61K 45/06; A61K 35/76; A61K 38/00; A61K 2039/505; A61P 35/00; A61P 31/04; A61P 33/06; C07K 7/06; C07K 7/08; C07K 14/70521; C07K 14/70532; C07K 16/2818; C07K 16/2827; C12N 15/00; Y02A 50/30

See application file for complete search history.

(56) References Cited

U.S. PATENT DOCUMENTS

| | | | |
|---|---|---|---|
| 10,098,950 | B2 | 10/2018 | Gutierrez et al. |
| 10,799,555 | B2 | 10/2020 | Gutierrez et al. |
| 10,799,581 | B2 | 10/2020 | Gutierrez et al. |
| 2002/0111323 | A1 | 8/2002 | Martin et al. |
| 2011/0203015 | A1 | 8/2011 | Sampson et al. |
| 2011/0318373 | A1 | 12/2011 | Sasikumar et al. |
| 2013/0017403 | A1 | 1/2013 | Huang et al. |
| 2013/0071403 | A1 | 3/2013 | Rolland et al. |
| 2013/0237580 | A1 | 9/2013 | Sasikumar et al. |
| 2015/0125955 | A1 | 5/2015 | Chomont et al. |
| 2016/0130345 | A1 | 5/2016 | Fotin-Mleczek et al. |
| 2017/0182150 | A1 | 6/2017 | Kallen et al. |
| 2017/0274074 | A1 | 9/2017 | Das-Young et al. |

FOREIGN PATENT DOCUMENTS

| | | | | |
|---|---|---|---|---|
| CN | 107383174 | A | 11/2017 | |
| WO | WO-9800546 | A2 * | 1/1998 | .......... C07K 14/325 |
| WO | 9842752 | A1 | 10/1998 | |
| WO | 2012168944 | A1 | 12/2012 | |
| WO | 2013144704 | A1 | 10/2013 | |
| WO | 2014127917 | A1 | 8/2014 | |
| WO | 2014209804 | A1 | 12/2014 | |
| WO | WO-2015024667 | A1 * | 2/2015 | ............ A61K 38/00 |
| WO | 2016061133 | A1 | 4/2016 | |

(Continued)

OTHER PUBLICATIONS

Peptide Atlas (CRRTSTGQISTLRVNITAPLSQ) 1 page. Nov. 4, 2023.*

(Continued)

*Primary Examiner* — Alana Harris Dent
(74) *Attorney, Agent, or Firm* — Banner & Witcoff, Ltd.

(57) ABSTRACT

This disclosure provides peptides which have a strong affinity for the checkpoint receptor "programmed death 1" (PD-1). These peptides block the interaction of PD-1 with its ligand PD-L1 as well as the interaction of CTLA4 with CD86 and can therefore be used for various therapeutic purposes, such as inhibiting the progression of a hyperproliferative disorder, including cancer; treating infectious diseases; enhancing a response to vaccination; treating sepsis; and promoting hair re-pigmentation or lightening of pigmented skin lesions.

13 Claims, 12 Drawing Sheets

Specification includes a Sequence Listing.

(56) References Cited

FOREIGN PATENT DOCUMENTS

| | | | |
|---|---|---|---|
| WO | 2017023753 | A1 | 2/2017 |
| WO | 2018053218 | A1 | 3/2018 |
| WO | 2018218137 | | 11/2018 |

OTHER PUBLICATIONS

Phares et al. (Frontiers in Immunology 11(1377): 1-11, Jul. 2020).*
Paul F. Agris. The importance of being modified: an unrealized code to RNA structure and function. RNA, 21: 552-554, 2015.*
Chang et al., "Blocking of the PD-1/PD-L1 Interaction by a D-Peptide Antagonist for Cancer Immunotherapy," Angedwandte Chemie International Edition 54, 11760-64, 2015.
Duraiswamy et al., "Dual Blockade of PD-1 and CTLA-4 Combined with Tumor Vaccine Effectively Restores T-Cell Rejection Function in Tumors," Cancer Res. 73, 3591-603, 2013.
International Search Report and Written Opinion for PCT/US2018/034625, Sep. 6, 2018, 15 pages.
Peptide Atlas searches, SEQ ID No. 1, 2 pages, Oct. 1, 2020, CRRTSTGQISTLRVNITAPLSQ.
Peptide Atlas searches, SEQ ID No. 8, 2 pages, Oct. 7, 2020, QISTLRVNITA.
Young et al., "Co-inhibition of CD73 and A2AR Adenosine Signaling Improves Anti-tumor Immune Responses," Cancer Cell 30, 391-403, 2016.
Zarganes-Tzitzikas et al., "Inhibitors of programmed cell death 1 (PD-1): a patent review," Expert Opinion on Therapeutic Patents 26, 973-77, published on-line Jul. 6, 2016.
Zhan et al., "From monoclonal antibodies to small molecules: the development of inhibitors targeting the PD-1/PD-L1 pathway," Drug Discovery Today 21, 1027-36, Jun. 2016.
Adams et al., "Big opportunities for small molecules in immuno-oncology," Nature Reviews Drug Discovery Advance Online Publication, Jul. 31, 2016, 20 pages.
Bruno et al., "Basics and recent advances in peptide and protein drug delivery," Ther. Deliv. 4, 1443-67, 2013.
Bu et al., "Learning from PD-1 Resistance: New Combination Strategies," Trends Mol. Med. 22, 448-51, 2016.
Burnett & Rossi, "RNA-based Therapeutics—Current Progress and Future Prospects," Chem Biol. 19, 60-71, 2012.
Cao, "Advances in Delivering Protein and Peptide Therapeutics," Pharmaceutical Technology 40, 22-24, Nov. 2, 2016.
Chang et al., "Blocking of the PD-1/PD-L1 Interaction by a D-Peptide Antagonist for Cancer Immunotherapy," Angew. Chem. Int. Ed. 54, 11760-64, 2015.
Cherkassky et al., "Human CAR T cells with cell-intrinsic PD-1 checkpoint blockade resist tumor-mediated inhibition," J. Clin. Invest. 126, 3130-44, 2016.
Chong et al., "PD-1 blockade modulates chimeric antigen receptor (CAR)-modified T cells: refueling the CAR," Blood. 129(8), 1039-41, 2017, published on-line Dec. 28, 2016.
Creative Biolabs User Manual, "TriCo-20TM Phage Display 20-mer Random Peptide Library," 14 pages, Aug. 4, 2009.
Differding, "AUNP-12—A Novel Peptide Therapeutic Targeting PD-1 Immune Checkpoint Pathway for Cancer Immunotherapy—Structure Activity Relationships & Peptide/Peptidomimetic Analogs," available at http://www.differding.com/data/AUNP_12_A_novel_peptide_therapeutic_targeting_PD_1_immune_checkpoint_pathway_for_cancer_immunotherapy.pdf, Feb. 26, 2014.
Feridooni et al., "Noninvasive Strategies for Systemic Delivery of Therapeutic Proteins—Prospects and Challenges," Chapter 8 of Sezer, ed., Smart Drug Delivery System, available at http://www.intechopen.com/books/smart-drug-delivery-system, Feb. 10, 2016.
Gutierrez et al., International Search Report and Written Opinion for PCT/US2015/051697, 5 pages, searched Nov. 13, 2017, mailed Dec. 1, 2017.
Gutierrez et al., PCT/US2015/051697 filed Sep. 15, 2017, 49 pages.
Gutierrez et al., U.S. Appl. No. 15/705,333, filed Sep. 15, 2017, 49 pages.
Gutierrez et al., U.S. Appl. No. 15/705,333 Interview Summary, Notice of Allowance, and Notice of Allowability dated Dec. 6, 2017, 18 pages.
Gutierrez et al., U.S. Appl. No. 15/705,333, amendment filed Feb. 28, 2018, 6 pages.
Gutierrez et al., U.S. Appl. No. 15/705,333, filed Feb. 27, 2018 continuation-in-part application of U.S. Appl. No. 15/705,333, filed Feb. 27, 2018, 63 pages.
Gutierrez et al., U.S. Appl. No. 15/906,481, Notice of Allowance dated Jun. 9, 2020, 8 pages.
Gutierrez et al., U.S. Appl. No. 15/906,481, Response to Restriction Requirement filed May 26, 2020, 5 pages.
Gutierrez et al., U.S. Appl. No. 15/705,333, filed Mar. 1, 2018 divisional application of U.S. Appl. No. 15/705,333, filed Mar. 1, 2018, 49 pages.
Gutierrez et al., U.S. Appl. No. 15/908,861, Notice of Allowance dated Jun. 12, 2020, 8 pages.
Gutierrez et al., U.S. Appl. No. 15/908,861, Response to Restriction Requirement filed May 26, 2020, 5 pages.
Gutierrez et al., U.S. Appl. No. 17/015,658, filed Sep. 9, 2020.
Gutierrez et al., U.S. Appl. No. 17/026,447, filed Sep. 21, 2020, 49 pages.
Gutierrez et al., U.S. Appl. No. 17/337,489 Application filed Jun. 3, 2021.
Gutierrez et al., U.S. Appl. No. 17/337,489 Preliminary Amendment filed Jun. 28, 2021.
Gutierrez et al., U.S. Appl. No. 17/337,489 Restriction Requirement dated Jan. 6, 2022.
Gutierrez et al., U.S. Appl. No. 17/497,069 Appliccation filed Oct. 8, 2021.
International Search Report and Written Opinion—International Patent Application No. PCT/US2021/054127, dated Oct. 8, 2021 (29 pages).
International Search Report and Written Opinion for PCT/US2018/020209, Oct. 22, 2018, 17 pages.
John et al., "Blockade of PD-1 immunosuppression boosts CAR T-cell therapy," OncoImmunology 2, e26286, 3 pages, 2013.
Kaczmarek et al., "Advances in the delivery of RNA therapeutics: from concept to clinical reality," Genome Medicine 2017; 9:60, 16 pages.
Kavikansky & Pavlick, "Beyond Checkpoint Inhibitors: The Next Generation of Immunotherapy in Oncology," Amer. J. Hematol. Oncol. 13, 9-20, 2017.
Kontermann, "Half-life extended biotherapeutics," Expert Opin. Biol. Ther. 16, 903-15, 2016.
Li et al., "Discovery of peptide inhibitors targeting human programmed death 1 (PD-1) receptor," Oncotarget 7, 64967-76, Aug. 12, 2016.
Magiera-Mularz et al., "Bioactive macrocyclic inhibitors of the PD-1/PD-L1 immune checkpoint," Angewandte Chemie Int. Ed. 10.1002/anie.201707707, e-published Sep. 26, 2017.
Maute et al., "Engineering high-affinity PD-1 variants for optimized immunotherapy and immuno-PET imaging," Proc. Natl. Acad. Sci. USA, E6506-E6514, published online Nov. 10, 2015.
Morrissey et al., "Immunotherapy and Novel Combinations in Oncology: Current Landscape, Challenges, and Opportunities," Clinical and Translational Science 9, 89-104, 2016.
Patel et al., "Recent Advances in Protein and Peptide Drug Delivery: A Special Emphasis on Polymeric Nanoparticles," Protein. Pept. Lett. 21, 1102-20, 2014.
Penchala et al., "A biomimetic approach for enhancing the in vivo half-life of peptides," Nat. Chem. Biol. 11, 793-98, 2015.
Phares et al., "Enhancement of the immune response to plasmodium yoelii circumsporozoite protein by PD-1 inhibitors," Amer. J. Tropical Med. and Hygiene 97, Abstract No. 1062, Nov. 1, 2017, 1 page.
Rivera et al., "Hair Repigmentation During Immunotherapy Treatment With an Anti-Programmed Cell Death 1 and Anti-Programmed Cell Death Ligand 1 Agent for Lung Cancer," JAMA Dermatol. Jul. 12, 2017. doi: 10.1001/iamadermatol.2017.2106, Jul. 12, 2017.
Sharma & Allison, "Immune Checkpoint Targeting in Cancer Therapy: Toward Combination Strategies with Curative Potential," Cell 161, 205-14, 2015.

(56) References Cited

OTHER PUBLICATIONS

Shindo et al., "Combination Immunotherapy with 4-1BB Activation and PD-1 Blockade Enhances Antitumor Efficacy in a Mouse Model of Subcutaneous Tumor," Anticancer Res. 35, 129-36, 2015.
Skalniak et al., "Small-molecule inhibitors of PD-1/PD-L1 immune checkpoint alleviate the PD-L1-induced exhaustion of T-cells," Oncotarget, Advance Publications, Aug. 7, 2017, 15 pages.
Smith, "Pigmented skin lesions lightened during melanoma immunotherapy," http://www.mdedge.com/edermatologynews/article/132598/melanoma/pigmented-skin-lesions-lightened-during-melanoma, Mar. 2, 2017.
Tzeng et al., "PD-1 blockage reverses immune dysfunction and hepatitis B viral persistence in a mouse animal model," PLoS One 7(6):e39179, 2012.
Van Dessel et al., "Potent and tumor specific: arming bacteria with therapeutic proteins," Ther. Deliv. 6, 385-99, 2015.
Yang et al., "Oral vaccination with *Salmonella* simultaneously expressing Yersinia pestis F1 and V antigens protects against bubonic and pneumonic plague," J Immunol. 178, 1059-67, 2007.
Ye et al., "T-cell exhaustion in chronic hepatitis B infection: current knowledge and clinical significance," Cell Death Dis. Mar. 19;6:e1694, 2015.
Al-Azzam et al., "Peptides to combat viral infectious diseases," Peptides 134, 170402, 2020.
Gutierrez et al., U.S. Appl. No. 17/015,658 Notice of Allowance dated Jul. 28, 2023.
Gutierrez et al., U.S. Appl. No. 17/026,447 Non-Final Office Action dated Jun. 8, 2023.
International Search Report and Written Opinion for PCT/US2021/054127, Apr. 13, 2023, 7 pages.
Ma et al., "Comparative genomics reveals mobile pathogenicity chromosomes in Fusarium", Nature, vol. 464, No. 7287, Mar. 18, 2010 (Mar. 18, 2010), pp. 367-373, XP055357917; & Ma et al., "hypothetical protein FOXG_05320 [*Fusarium oxysporum* f. sp. *sycopersici*—Protein—NCBI", nature, Sep. 26, 2016 (Sep. 26, 2016), XP055879013, Retrieved from the Internet: URL:https://www.ncbi.nlm.nih.gov/protein/XP_018240489.
Seif et al., "CAR T Cells Beyond Cancer: Hope for Immunomodulatory Therapy of Infectious Diseases," Frontiers in Immunology, vol. 10, Article 2711, 2019.

* cited by examiner

SEQUENCE LISTING

```
<160> NUMBER OF SEQ ID NOS: 38

<210> SEQ ID NO 1
<211> LENGTH: 22
<212> TYPE: PRT
<213> ORGANISM: Artificial Sequence
<220> FEATURE:
<223> OTHER INFORMATION: LD01 peptide
<221> NAME/KEY: AMIDATION
<222> LOCATION: (22)...(22)

<400> SEQUENCE: 1
```

-continued

```
Cys Arg Arg Thr Ser Thr Gly Gln Ile Ser Thr Leu Arg Val Asn Ile
1               5                   10                  15

Thr Ala Pro Leu Ser Gln
            20


<210> SEQ ID NO 2
<211> LENGTH: 21
<212> TYPE: PRT
<213> ORGANISM: Bacillus thuringiensis
<220> FEATURE:
<223> OTHER INFORMATION: LD02 peptide

<400> SEQUENCE: 2

Arg Arg Thr Ser Pro Gly Gln Ile Ser Thr Leu Arg Val Asn Ile Thr
1               5                   10                  15

Ala Pro Leu Ser Gln
            20


<210> SEQ ID NO 3
<211> LENGTH: 22
<212> TYPE: PRT
<213> ORGANISM: Artificial Sequence
<220> FEATURE:
<223> OTHER INFORMATION: LD12 peptide

<400> SEQUENCE: 3

Cys Arg Arg Thr Ser Thr Gly Gln Ile Ser Thr Ala Arg Val Asn Ile
1               5                   10                  15

Thr Ala Pro Leu Ser Gln
            20


<210> SEQ ID NO 4
<211> LENGTH: 22
<212> TYPE: PRT
<213> ORGANISM: Artificial Sequence
<220> FEATURE:
<223> OTHER INFORMATION: LD12a peptide
<221> NAME/KEY: AMIDATION
<222> LOCATION: (22)...(22)

<400> SEQUENCE: 4

Cys Arg Arg Thr Ser Thr Gly Gln Ile Ser Thr Ala Arg Val Asn Ile
1               5                   10                  15

Thr Ala Pro Leu Ser Gln
            20


<210> SEQ ID NO 5
<211> LENGTH: 22
<212> TYPE: PRT
<213> ORGANISM: Artificial Sequence
<220> FEATURE:
<223> OTHER INFORMATION: LD11 peptide

<400> SEQUENCE: 5

Cys His His Thr Ser Thr Gly Gln Ile Ser Thr Leu Arg Val Asn Ile
1               5                   10                  15

Thr Ala Pro Leu Ser Gln
            20


<210> SEQ ID NO 6
<211> LENGTH: 21
<212> TYPE: PRT
<213> ORGANISM: Artificial Sequence
<220> FEATURE:
<223> OTHER INFORMATION: LD03 peptide
```

<400> SEQUENCE: 6

Val Val Lys Gly Pro Gly Phe Thr Gly Gly Asp Ile Leu Arg Arg Thr
1 5 10 15

Ser Pro Gly Gln Ile
20

<210> SEQ ID NO 7
<211> LENGTH: 20
<212> TYPE: PRT
<213> ORGANISM: Bacillus thuringiensis
<220> FEATURE:
<223> OTHER INFORMATION: LD04 peptide

<400> SEQUENCE: 7

Ser Thr Leu Arg Val Asn Ile Thr Ala Pro Leu Ser Gln Arg Tyr Arg
1 5 10 15

Val Arg Ile Arg
20

<210> SEQ ID NO 8
<211> LENGTH: 11
<212> TYPE: PRT
<213> ORGANISM: Bacillus thuringiensis
<220> FEATURE:
<223> OTHER INFORMATION: LD40 peptide

<400> SEQUENCE: 8

Gln Ile Ser Thr Leu Arg Val Asn Ile Thr Ala
1 5 10

<210> SEQ ID NO 9
<211> LENGTH: 8
<212> TYPE: PRT
<213> ORGANISM: Artificial Sequence
<220> FEATURE:
<223> OTHER INFORMATION: LD41 peptide

<400> SEQUENCE: 9

Ser Thr Leu Arg Ile Asn Thr Thr
1 5

<210> SEQ ID NO 10
<211> LENGTH: 9
<212> TYPE: PRT
<213> ORGANISM: Artificial Sequence
<220> FEATURE:
<223> OTHER INFORMATION: LD42 peptide

<400> SEQUENCE: 10

Ser Thr Leu Arg Gly Ser Thr Thr Ala
1 5

<210> SEQ ID NO 11
<211> LENGTH: 15
<212> TYPE: PRT
<213> ORGANISM: Oryza brachyantha
<220> FEATURE:
<223> OTHER INFORMATION: LD01r peptide

<400> SEQUENCE: 11

Arg Thr Ser Thr Gly Asp Ile Thr Ser Leu Arg Val Ile Thr Ala
1 5 10 15

<210> SEQ ID NO 12

-continued

<211> LENGTH: 18
<212> TYPE: PRT
<213> ORGANISM: Artificial Sequence
<220> FEATURE:
<223> OTHER INFORMATION: LD10 peptide

<400> SEQUENCE: 12

Ser Thr Gly Gln Ile Ser Thr Leu Arg Val Asn Ile Thr Ala Pro Leu
1 5 10 15

Ser Gln

<210> SEQ ID NO 13
<211> LENGTH: 18
<212> TYPE: PRT
<213> ORGANISM: Artificial Sequence
<220> FEATURE:
<223> OTHER INFORMATION: LD10 Q4A peptide

<400> SEQUENCE: 13

Ser Thr Gly Ala Ile Ser Thr Leu Arg Val Asn Ile Thr Ala Pro Leu
1 5 10 15

Ser Gln

<210> SEQ ID NO 14
<211> LENGTH: 18
<212> TYPE: PRT
<213> ORGANISM: Artificial Sequence
<220> FEATURE:
<223> OTHER INFORMATION: LD10 T7A peptide

<400> SEQUENCE: 14

Ser Thr Gly Gln Ile Ser Ala Leu Arg Val Asn Ile Thr Ala Pro Leu
1 5 10 15

Ser Gln

<210> SEQ ID NO 15
<211> LENGTH: 18
<212> TYPE: PRT
<213> ORGANISM: Artificial Sequence
<220> FEATURE:
<223> OTHER INFORMATION: LD10 R9A peptide

<400> SEQUENCE: 15

Ser Thr Gly Gln Ile Ser Thr Leu Ala Val Asn Ile Thr Ala Pro Leu
1 5 10 15

Ser Gln

<210> SEQ ID NO 16
<211> LENGTH: 18
<212> TYPE: PRT
<213> ORGANISM: Artificial Sequence
<220> FEATURE:
<223> OTHER INFORMATION: LD10 N11A peptide

<400> SEQUENCE: 16

Ser Thr Gly Gln Ile Ser Thr Leu Arg Val Ala Ile Thr Ala Pro Leu
1 5 10 15

Ser Gln

<210> SEQ ID NO 17
<211> LENGTH: 18
<212> TYPE: PRT
<213> ORGANISM: Artificial Sequence
<220> FEATURE:

<223> OTHER INFORMATION: LD10 P15A peptide

<400> SEQUENCE: 17

Ser Thr Gly Gln Ile Ser Thr Leu Arg Val Asn Ile Thr Ala Ala Leu
1 5 10 15

Ser Gln

<210> SEQ ID NO 18
<211> LENGTH: 18
<212> TYPE: PRT
<213> ORGANISM: Artificial Sequence
<220> FEATURE:
<223> OTHER INFORMATION: LD10 L8A peptide

<400> SEQUENCE: 18

Ser Thr Gly Gln Ile Ser Thr Ala Arg Val Asn Ile Thr Ala Pro Leu
1 5 10 15

Ser Gln

<210> SEQ ID NO 19
<211> LENGTH: 18
<212> TYPE: PRT
<213> ORGANISM: Artificial Sequence
<220> FEATURE:
<223> OTHER INFORMATION: LD10 L16A peptide

<400> SEQUENCE: 19

Ser Thr Gly Gln Ile Ser Thr Leu Arg Val Asn Ile Thr Ala Pro Ala
1 5 10 15

Ser Gln

<210> SEQ ID NO 20
<211> LENGTH: 18
<212> TYPE: PRT
<213> ORGANISM: Artificial Sequence
<220> FEATURE:
<223> OTHER INFORMATION: LD10 T13A peptide

<400> SEQUENCE: 20

Ser Thr Gly Gln Ile Ser Thr Leu Arg Val Asn Ile Ala Ala Pro Leu
1 5 10 15

Ser Gln

<210> SEQ ID NO 21
<211> LENGTH: 18
<212> TYPE: PRT
<213> ORGANISM: Artificial Sequence
<220> FEATURE:
<223> OTHER INFORMATION: LD17 peptide
<221> NAME/KEY: AMIDATION
<222> LOCATION: (18)...(18)

<400> SEQUENCE: 21

Ser Thr Gly Gln Ile Ser Thr Leu Arg Val Asn Ile Thr Ala Pro Leu
1 5 10 15

Ser Gln

<210> SEQ ID NO 22
<211> LENGTH: 18
<212> TYPE: PRT
<213> ORGANISM: Artificial Sequence
<220> FEATURE:
<223> OTHER INFORMATION: LD17m peptide
<221> NAME/KEY: AMIDATION

<222> LOCATION: (18)...(18)

<400> SEQUENCE: 22

Ser Thr Gly Gln Ile Ser Thr Ala Arg Val Asn Ile Thr Ala Pro Leu
1 5 10 15

Ser Gln

<210> SEQ ID NO 23
<211> LENGTH: 18
<212> TYPE: PRT
<213> ORGANISM: Artificial Sequence
<220> FEATURE:
<223> OTHER INFORMATION: LD10aa peptide
<221> NAME/KEY: ACETYLATION
<222> LOCATION: (1)...(1)
<221> NAME/KEY: AMIDATION
<222> LOCATION: (18)...(18)

<400> SEQUENCE: 23

Ser Thr Gly Gln Ile Ser Thr Leu Arg Val Asn Ile Thr Ala Pro Leu
1 5 10 15

Ser Gln

<210> SEQ ID NO 24
<211> LENGTH: 18
<212> TYPE: PRT
<213> ORGANISM: Artificial Sequence
<220> FEATURE:
<223> OTHER INFORMATION: LD10da peptide
<221> NAME/KEY: AMIDATION
<222> LOCATION: (18)...(18)
<221> NAME/KEY: UNSURE
<222> LOCATION: (1)...(1)
<223> OTHER INFORMATION: D-amino acid

<400> SEQUENCE: 24

Ser Thr Gly Gln Ile Ser Thr Leu Arg Val Asn Ile Thr Ala Pro Leu
1 5 10 15

Ser Gln

<210> SEQ ID NO 25
<211> LENGTH: 18
<212> TYPE: PRT
<213> ORGANISM: Artificial Sequence
<220> FEATURE:
<223> OTHER INFORMATION: LD10 da m peptide
<221> NAME/KEY: AMIDATION
<222> LOCATION: (18)...(18)
<221> NAME/KEY: UNSURE
<222> LOCATION: (1)...(1)
<223> OTHER INFORMATION: D-amino acid

<400> SEQUENCE: 25

Ser Thr Gly Gln Ile Ser Thr Ala Arg Val Asn Ile Thr Ala Pro Leu
1 5 10 15

Ser Gln

<210> SEQ ID NO 26
<211> LENGTH: 19
<212> TYPE: PRT
<213> ORGANISM: Artificial Sequence
<220> FEATURE:
<223> OTHER INFORMATION: LD16 peptide

<400> SEQUENCE: 26

Thr Ser Thr Gly Gln Ile Ser Thr Leu Arg Val Asn Ile Thr Ala Pro

```
1               5                   10                  15

Leu Ser Gln


<210> SEQ ID NO 27
<211> LENGTH: 19
<212> TYPE: PRT
<213> ORGANISM: Artificial Sequence
<220> FEATURE:
<223> OTHER INFORMATION: LD01 TQ19 peptide
<221> NAME/KEY: AMIDATION
<222> LOCATION: (19)...(19)

<400> SEQUENCE: 27

Thr Ser Thr Gly Gln Ile Ser Thr Leu Arg Val Asn Ile Thr Ala Pro
1               5                   10                  15

Leu Ser Gln


<210> SEQ ID NO 28
<211> LENGTH: 19
<212> TYPE: PRT
<213> ORGANISM: Artificial Sequence
<220> FEATURE:
<223> OTHER INFORMATION: LD16m peptide
<221> NAME/KEY: AMIDATION
<222> LOCATION: (19)...(19)

<400> SEQUENCE: 28

Thr Ser Thr Gly Gln Ile Ser Thr Ala Arg Val Asn Ile Thr Ala Pro
1               5                   10                  15

Leu Ser Gln


<210> SEQ ID NO 29
<211> LENGTH: 19
<212> TYPE: PRT
<213> ORGANISM: Artificial Sequence
<220> FEATURE:
<223> OTHER INFORMATION: LD01 TQ19 aa peptide
<221> NAME/KEY: ACETYLATION
<222> LOCATION: (1)...(1)
<221> NAME/KEY: AMIDATION
<222> LOCATION: (19)...(19)

<400> SEQUENCE: 29

Thr Ser Thr Gly Gln Ile Ser Thr Leu Arg Val Asn Ile Thr Ala Pro
1               5                   10                  15

Leu Ser Gln


<210> SEQ ID NO 30
<211> LENGTH: 19
<212> TYPE: PRT
<213> ORGANISM: Artificial Sequence
<220> FEATURE:
<223> OTHER INFORMATION: LD01 TQ19 da peptide
<221> NAME/KEY: UNSURE
<222> LOCATION: (1)...(1)
<223> OTHER INFORMATION: D-amino acid
<221> NAME/KEY: AMIDATION
<222> LOCATION: (19)...(19)

<400> SEQUENCE: 30

Thr Ser Thr Gly Gln Ile Ser Thr Leu Arg Val Asn Ile Thr Ala Pro
1               5                   10                  15

Leu Ser Gln


<210> SEQ ID NO 31
```

-continued

<211> LENGTH: 19
<212> TYPE: PRT
<213> ORGANISM: Artificial Sequence
<220> FEATURE:
<223> OTHER INFORMATION: LD01 TQ19 da m peptide
<221> NAME/KEY: UNSURE
<222> LOCATION: (1)...(1)
<223> OTHER INFORMATION: D-amino acid
<221> NAME/KEY: AMIDATION
<222> LOCATION: (19)...(19)

<400> SEQUENCE: 31

Thr Ser Thr Gly Gln Ile Ser Thr Ala Arg Val Asn Ile Thr Ala Pro
1 5 10 15

Leu Ser Gln

<210> SEQ ID NO 32
<211> LENGTH: 21
<212> TYPE: PRT
<213> ORGANISM: Bacillus thuringiensis
<220> FEATURE:
<223> OTHER INFORMATION: LD05 peptide

<400> SEQUENCE: 32

Met Phe Arg Ser Gly Phe Ser Asn Ser Ser Val Ser Ile Ile Arg Ala
1 5 10 15

Pro Met Phe Ser Trp
20

<210> SEQ ID NO 33
<211> LENGTH: 21
<212> TYPE: PRT
<213> ORGANISM: Mus musculus
<220> FEATURE:
<223> OTHER INFORMATION: myelin oligodendrocyte glycoprotein (MOG) peptide

<400> SEQUENCE: 33

Met Glu Val Gly Trp Tyr Arg Ser Pro Phe Ser Arg Val Val His Leu
1 5 10 15

Tyr Arg Asn Gly Lys
20

<210> SEQ ID NO 34
<211> LENGTH: 8
<212> TYPE: PRT
<213> ORGANISM: Mus musculus
<220> FEATURE:
<223> OTHER INFORMATION: ovalbumin (OVA) peptide

<400> SEQUENCE: 34

Ser Ile Ile Asn Phe Glu Lys Leu
1 5

<210> SEQ ID NO 35
<211> LENGTH: 9
<212> TYPE: PRT
<213> ORGANISM: Plasmodium yoelii
<220> FEATURE:
<223> OTHER INFORMATION: H-2Kd-restricted CD8+ T cell epitope

<400> SEQUENCE: 35

Ser Tyr Val Pro Ser Ala Glu Gln Ile
1 5

<210> SEQ ID NO 36

-continued

```
<211> LENGTH: 22
<212> TYPE: PRT
<213> ORGANISM: Artificial Sequence
<220> FEATURE:
<223> OTHER INFORMATION: peptide LD01(u)

<400> SEQUENCE: 36

Cys Arg Arg Thr Ser Thr Gly Gln Ile Ser Thr Leu Arg Val Asn Ile
1               5                   10                  15

Thr Ala Pro Leu Ser Gln
            20


<210> SEQ ID NO 37
<211> LENGTH: 18
<212> TYPE: PRT
<213> ORGANISM: Artificial Sequence
<220> FEATURE:
<223> OTHER INFORMATION: peptide LD17m(u)

<400> SEQUENCE: 37

Ser Thr Gly Gln Ile Ser Thr Ala Arg Val Asn Ile Thr Ala Pro Leu
1               5                   10                  15

Ser Gln


<210> SEQ ID NO 38
<211> LENGTH: 19
<212> TYPE: PRT
<213> ORGANISM: Artificial Sequence
<220> FEATURE:
<223> OTHER INFORMATION: peptide LD01 TQ19(u)

<400> SEQUENCE: 38

Thr Ser Thr Gly Gln Ile Ser Thr Leu Arg Val Asn Ile Thr Ala Pro
1               5                   10                  15

Leu Ser Gln
```

PD-1 AND CTLA-4 DUAL INHIBITOR PEPTIDES

This application is a division of Ser. No. 15/989,750 filed on May 25, 2018, which claims priority to and incorporates by reference U.S. provisional application Ser. No. 62/510,900 filed on May 25, 2017.

This application incorporates by reference the contents of a 10.0 kb text filed created on Apr. 30, 2021 and named "00047900285sequencelisting.txt," which is the sequence listing for this application.

Each scientific reference, patent, and published patent application cited in this disclosure is incorporated herein by reference in its entirety.

TECHNICAL FIELD

This disclosure relates generally to immunomodulatory peptides.

BACKGROUND

Programmed cell death-1 (PD-1) and its ligands, PD-L1 and PD-L2, are widely expressed and exert a number of immunoregulatory roles in T cell activation, including attenuation of immunity against tumor cells and infectious agents. PD-1 is therefore an attractive target for a variety of therapeutic applications. Cytotoxic T-lymphocyte-associated antigen (CTLA-4) provides a negative signal to T cells and is also an attractive therapeutic target. There is a continuing need for useful modulators of immune checkpoint pathways.

BRIEF DESCRIPTION OF THE FIGURES

FIG. 4A, low concentration range of peptide LD01. FIG. 4B, high concentration range of peptide LD01. FIG. 4C, peptide LD01.

DETAILED DESCRIPTION

Figure 1:
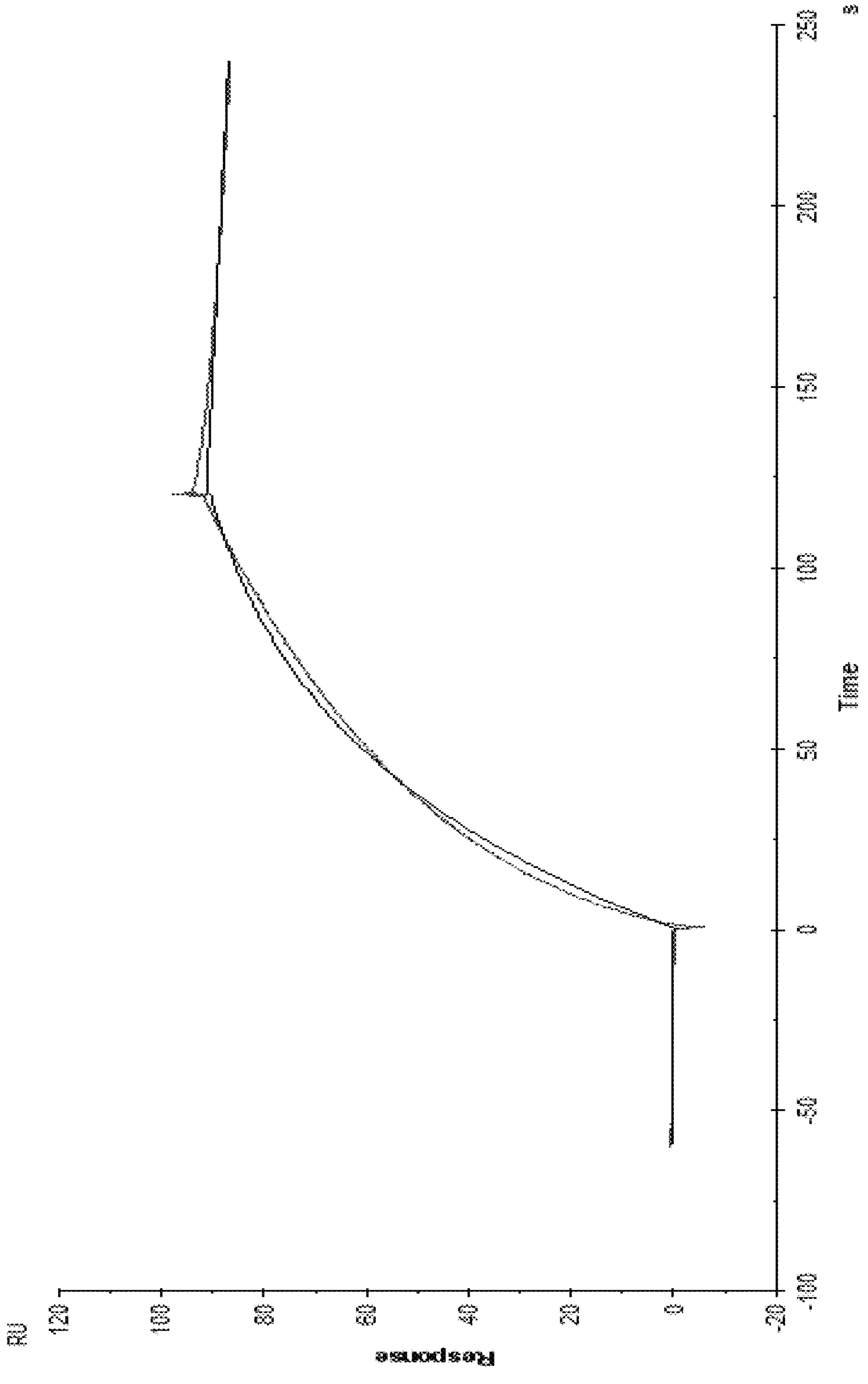
FIG. 1 is a graph providing single concentration BIACORE® data for peptide LD01 binding to human PD-1.

This disclosure provides peptides that block the interaction of the checkpoint receptor "programmed death 1" (PD-1) with its ligand PD-L1 and which also block the binding of CD86 to CTLA-4. In some embodiments, a disclosed peptide is modified using chemical or recombinant methods to enhance its stability or other pharmacokinetic properties. See, e.g., US 2017/0020956. Modifications include, but are not limited to, replacement of one or more L-amino acid with its corresponding D-form, acetylation on a C- and/or N-terminal residue, amidation on a C- and/or N-terminal residue, cyclization, esterification, glycosylation, acylation, attachment of myristic or palmitic acid, addition of an N-terminal glycine, addition of lipophilic moieties such as long fatty acid chains, and PEGylation.

Non-limiting examples of peptides and modified versions thereof are included in the table below, in which "$NH_2$" indicates C-terminal amidation, "$CH_3CO$" indicates N-terminal acetylation, and a lower case letter indicates the D form of the amino acid.

| peptide | amino acid sequence | SEQ ID NO: |
|---|---|---|
| LD01 | CRRTSTGQISTLRVNITAPLSQ-$NH_2$ | 1 |
| LD11 | CHHTSTGQISTLRVNITAPLSQ | 5 |
| LD04 | STLRVNITAPLSQRYRVRIR | 7 |
| LD40 | QISTLRVNITA | 8 |
| LD01r | RTSTGDITSLRVITA | 11 |
| LD10 | STGQISTLRVNITAPLSQ | 12 |
| LD10 R9A | STGQISTLAVNITAPLSQ | 15 |
| LD10 P15A | STGQISTLRVNITAALSQ | 17 |
| LD17 | STGQISTLRVNITAPLSQ-$NH_2$ | 21 |
| LD17m | STGQISTARVNITAPLSQ-$NH_2$ | 22 |
| LD10da | sTGQISTLRVNITAPLSQ-$NH_2$ | 24 |
| LD01 TQ19 | TSTGQISTLRVNITAPLSQ-$NH_2$ | 27 |
| LD01 TQ19aa | $CH_3CO$-TSTGQISTLRVNITAPLSQ-$NH_2$ | 29 |
| LD01 TQ19da/ LD16da | tSTGQISTLRVNITAPLSQ-$NH_2$ | 30 |
| LD01(u) | CRRTSTGQISTLRVNITAPLSQ | 36 |
| LD17m (u) | STGQISTARVNITAPLSQ | 37 |
| LD01 TQ19 (u) | TSTGQISTLRVNITAPLSQ | 38 |

Peptides can be made by any method known in the art, including synthetic methods, recombinant methods, or both. Synthetic methods include solid-phase and solution methods, and may include the use of protective groups. See, e.g., Bodanszky et al. (1976), McOmie (1973), Merrifield (1963), Neurath et al. (1976), Stuart & Young (1984).

Recombinant production of peptides can be carried out using any nucleotide sequence(s) encoding the peptides in any suitable expression system. Nucleic acid molecules encoding one or more of the disclosed peptides can be incorporated into an expression cassette that includes control elements operably linked to the coding sequences. Control elements include, but are not limited to, initiators, promoters (including inducible, repressible, and constitutive promoters), enhancers, and polyadenylation signals. Signal sequences can be included. The expression cassette can be provided in a vector that can be introduced into an appropriate host cell for production of the peptide(s). Methods of constructing expression cassettes and expression vectors are well known. Expression vectors can include one or more expression cassettes encoding one or more peptides comprising, consisting essentially or, or consisting of SEQ ID NO:5, 7, 8, 11, 12, 15, 17, 36, 37, 38, or 39.

In some embodiments, one or more peptides are expressed as a component of a fusion protein. Other components of the fusion protein can be, for example, a cytokine or an engineered T cell receptor (TCR). A fusion protein can comprise one or more linkers between its components. In some embodiments, a linker between a peptide and another component of the fusion protein can comprise a proteolytic cleavage site to release the peptide after expression of the fusion protein. See, e.g., US 2016/0138066; US 2018/0135060; US 2014/0343251; US 2012/0142891; Rodriguez et al., 2014.

In some embodiments, a component of a fusion protein is a moiety, such as albumin or transthyretin, which can enhance the plasma half-life of the peptide. In other embodiments, a peptide or a modified version of a peptide is conjugated to the moiety. Methods of preparing such conjugates are well known in the art (e.g., Penchala et al., 2015; Kontermann, 2016; Zorzi et al., 2017).

In some embodiments, a component of a fusion protein is a partner molecule, such as a peptide or protein such as an antibody intended to increase the half-life of a peptide or modified peptide in vivo and/or to provide specific delivery to a target tissue or cell. Alternatively, a peptide or modified version thereof can be conjugated to the partner molecule. Conjugation may be direct or can be via a linker. In some of these embodiments, a peptide or a modified version thereof can be altered to substitute one or more amino acids with amino acids used to attach partner molecules, such as lysine, or by N-terminal extension of the peptide with, e.g., 1, 2, 3, or 4 glycine spacer molecules.

This disclosure also provides CAR-T cells that express one or more of the disclosed peptides. Methods of preparing CAR-T cells are disclosed, for example, in U.S. Pat. Nos. 9,328,156; 9,845,362; and 9,101,584.

This disclosure also provides oncolytic viruses containing a nucleic acid molecule encoding one or more of the disclosed peptides. See US 2017/0157188; Lawler et al., 2017; US 2015/0250837. Oncolytic viruses include, but are not limited to, reovirus, Seneca Valley virus, vesicular stomatitis virus, Newcastle disease virus, *herpes simplex* virus, morbillivirus virus, retrovirus, influenza virus, Sindbis virus, poxvirus, and adenovirus.

Examples of oncolytic reovirus include REOLYSIN® (pelareorep) and reoviruses disclosed in US 2017/0049829.

Examples of oncolytic Seneca Valley virus include NTX-101 (Rudin et al., 2011).

Examples of oncolytic vesicular stomatitis virus are disclosed in Stojdl et al., 2000; and Stojdl et al., 2003.

Examples of oncolytic Newcastle disease virus include 73-T PV701 and HDV-HUJ strains (see also Phuangsab et al., 2001; Lorence et al., 2007; and Freeman et al., 2006).

Examples of oncolytic *herpes simplex* virus include NV1020 (Geevarghese et al., 2010) and T-VEC (Andtbacka et al., 2013).

Examples of oncolytic morbillivirus virus include oncolytic measles viruses such as MV-Edm (McDonald et al., 2006) and HMWMAA (Kaufmann et al., 2013).

Examples of oncolytic retrovirus are disclosed in Lu et al., 2012.

Examples of oncolytic influenza virus are disclosed, for example, in US 2018/0057594.

Examples of oncolytic Sindbis virus are disclosed, for example, in Lundstrom, 2017.

Examples of oncolytic poxvirus are disclosed, for example, in Chan & McFadden, 2014.

Examples of oncolytic adenovirus include ONYX-015 (Khuri et al., 2000) and H101 or Oncorine (Liang, 2018).

Therapeutic Uses

The peptides and modified versions thereof disclosed herein have a number of therapeutic applications, including treating hyperproliferative disorders, including cancer, treating infectious diseases, enhancing a response to vaccination, treating sepsis, promoting hair re-pigmentation, and promoting lightening of a pigmented skin lesion. "Treat," as used herein, includes reducing or inhibiting the progression of one or more symptoms of the condition for which a peptide or modified version thereof is administered.

"Administer" as used herein includes direct administration of a disclosed peptide or modified version thereof as well as indirect administration.

In some embodiments, one or more of the disclosed peptides and/or modified versions thereof, are directly administered. In some of these embodiments, a peptide carrier system is used. A number of peptide carrier systems are known in the art, including microparticles, polymeric nanoparticles, liposomes, solid lipid nanoparticles, hydrophilic mucoadhesive polymers, thiolated polymers, polymer matrices, nanoemulsions, and hydrogels. See Patel et al. (2014), Bruno et al. (2013), Feridooni et al. (2016). Any suitable system can be used.

In some embodiments, an engineered T cell that expresses and secretes one or more disclosed peptides can be used to deliver PD-1 inhibition at the site of engagement of the T cell receptor with an antigen. The T cell-based therapy can be, for example, a CAR-T cell that expresses one or more of the disclosed peptides. Either inducible or constitutive expression can be used.

In some embodiments, an oncolytic virus can be used to deliver one or more of the disclosed peptides. Either inducible or constitutive expression can be used.

In other embodiments one or more of the disclosed peptides are delivered using one or more nucleic acids encoding the peptide(s) (e.g., DNA, cDNA, PNA, RNA or a combination thereof); see, e.g., US 2017/0165335. Nucleic acids encoding one or more peptides can be delivered using a variety of delivery systems known in the art. Nucleic acid delivery systems include, but are not limited to, gene-gun; cationic lipids and cationic polymers; encapsulation in liposomes, microparticles, or microcapsules; electroporation; virus-based, and bacterial-based delivery systems. Virus-based systems include, but are not limited to, modified viruses such as adenovirus, adeno-associated virus, *herpes* virus, retroviruses, vaccinia virus, or hybrid viruses containing elements of one or more viruses. US 2002/0111323 describes use of "naked DNA," i.e., a "non-infectious, non-immunogenic, non-integrating DNA sequence," free from "transfection-facilitating proteins, viral particles, liposomal formulations, charged lipids and calcium phosphate precipitating agents," to administer a peptide. Bacterial-based delivery systems are disclosed, e.g., in Van Dessel et al. (2015) and Yang et al. (2007).

In some embodiments, a peptide is administered via an RNA molecule encoding the peptide. In some embodiments, the RNA molecule is encapsulated in a nanoparticle. In some embodiments, the nanoparticle comprises a cationic polymer (e.g., poly-L-lysine, polyamidoamine, polyethyleneimine, chitosan, poly(O-amino esters). In some embodiments, the nanoparticle comprises a cationic lipid or an ionizable lipid. In some embodiments, the RNA molecule is conjugated to a bioactive ligand (e.g., N-acetylgalactosamine (GalNAc), cholesterol, vitamin E, antibodies, cell-penetrating peptides). See, e.g., Akinc et al. (2008), Akinc et al. (2009), Anderson et al. (2003), Behr (1997), Boussif et al. (1995), Chen et al. (2012), Dahlman et al. (2014), Desigaux et al. (2007), Dong et al. (2014), Dosta et al. (2015), Fenton et al. (2016), Guo et al. (2012), Howard et al. (2006), Kaczmarek et al. (2016), Kanasty et al. (2013), Kauffman et al. (2015), Kozielski et al. (2013), Leus et al. (2014), Lorenz et al. (2004), Love et al. (2010), Lynn & Langer (2000), Moschos et al. (2007), Nair et al. (2014), Nishina et al. (2008), Pack et al. (2005), Rehman et al. (2013), Schroeder et al. (2010), Tsutsumi et al. (2007), Tzeng et al. (2012), Won et al. (2009), Xia et al. (2009), Yu et al. (2016).

In some embodiments, an RNA molecule can be modified to reduce its chances of degradation or recognition by the immune system. The ribose sugar, the phosphate linkage, and/or individual bases can be modified. See, e.g., Behlke (2008), Bramsen (2009), Chiu (2003), Judge & MacLachlan (2008), Kauffman (2016), Li (2016), Morrissey (2005), Prakash (2005), Pratt & MacRae (2009), Sahin (2014), Soutschek (2004), Wittrup & Lieberman (2015). In some embodiments, the modification is one or more of a ribo-difluorotoluyl nucleotide, a 4'-thio modified RNA, a boranophosphate linkage, a phosphorothioate linkage, a 2'-O-methyl (2'-OMe) sugar substitution, a 2'-fluoro (2'-F), a 2'-O-methoxyethyl (2'-MOE) sugar substitution, a locked nucleic acid (LNA), and an L-RNA.

In some embodiments, administration is carried out in conjunction with one or more other therapies. "In conjunction with" includes administration together with, before, or after administration of the one or more other therapies.

Pharmaceutical Compositions, Routes of Administration, and Devices

One or more peptides, modified peptides, nucleic acid molecules, CAR-T cells, and/or oncolytic viruses, as discussed above, are typically administered in a pharmaceutical composition comprising a pharmaceutically acceptable vehicle. The "pharmaceutically acceptable vehicle" may comprise one or more substances which do not affect the biological activity of the peptides or modified versions thereof and, when administered to a patient, does not cause an adverse reaction. Pharmaceutical compositions may be liquid or may be lyophilized. Lyophilized compositions may be provided in a kit with a suitable liquid, typically water for injection (WFI) for use in reconstituting the composition. Other suitable forms of pharmaceutical compositions include suspensions, emulsions, and tablets.

Pharmaceutical compositions can be administered by any suitable route, including, but not limited to, intravenous, intramuscular, intradermal, intraperitoneal, subcutaneous, epidural, intratumoral, transdermal (e.g., US 2017/0281672), mucosal (e.g., intranasal or oral), pulmonary, and topical (e.g., US 2017/0274010) routes. See, e.g., US 2017/0101474.

Administration can be systemic or local. In addition to local infusions and injections, implants can be used to achieve a local administration. Examples of suitable materials include, but are not limited to, sialastic membranes, polymers, fibrous matrices, and collagen matrices.

Topical administration can be by way of a cream, ointment, lotion, transdermal patch (such as a microneedle patch), or other suitable forms well known in the art.

Administration can also be by controlled release, for example, using a microneedle patch, pump and/or suitable polymeric materials. Examples of suitable materials include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters.

Devices comprising any of the peptides, modified peptides, nucleic acid molecules, CAR-T cells, and/or oncolytic viruses described above include, but are not limited to, syringes, pumps, transdermal patches, spray devices, vaginal rings, and pessaries.

Treatment of Hyperproliferative Disorders, Including Cancer

In some embodiments, one or more of the peptides, modified peptides, nucleic acid molecules, CAR-T cells, and/or oncolytic viruses described above are administered to a patient to inhibit the progression of a hyperproliferative disorder, including cancer. Such inhibition may include, for example, reducing proliferation of neoplastic or pre-neoplastic cells; destroying neoplastic or pre-neoplastic cells; and inhibiting metastasis or decreasing the size of a tumor.

Examples of cancers include, but are not limited to, melanoma (including cutaneous or intraocular malignant melanoma), renal cancer, prostate cancer, breast cancer, colon cancer, lung cancer, bone cancer, pancreatic cancer, skin cancer, cancer of the head or neck, uterine cancer, ovarian cancer, rectal cancer, cancer of the anal region, stomach cancer, testicular cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, and T-cell lymphoma.

Combination Cancer Therapies

In some embodiments, one or more of the peptides, modified peptides, nucleic acid molecules, CAR-T cells, and/or oncolytic viruses described above are administered in conjunction with one or more other cancer therapies or immunotherapies, such as those described below.

In some embodiments, the second therapy comprises a second agent that reduces or blocks the activity of PD-1 (e.g., nivolumab, pembrolizumab, durvalumab) or CTLA-4 (e.g., ipilimumab, tremelimumab).

In some embodiments, the second therapy comprises an agent that reduces or blocks the activity of PD-L1 (e.g., atezolizumab).

In some embodiments, the second therapy comprises an agent that reduces or blocks the activity of other inhibitory checkpoint molecules and/or molecules that suppress the immune system. These molecules include, but are not limited to:

1. Lymphocyte-activation gene-3 (LAG-3; see He et al., 2016; Triebel et al., 1990);
2. V-domain Immunoglobulin Suppressor of T cell Activation (VISTA, also known as c10orf54, PD-1H, DD1α, Gi24, Diesi, and SISP1; see US 2017/0334990, US 2017/0112929, Gao et al., 2017, Wang et al., 2011; Liu et al., 2015);
3. T-cell Immunoglobulin domain and Mucin domain 3 (TIM-3; see US 2017/0198041, US 2017/0029485, US 2014/0348842, Sakuishi et al., 2010);
4. killer immunoglobulin-like receptors (KIRs; see US 2015/0290316);
5. agents that inhibit indoleamine (2,3)-dioxygenase (IDO; see Mellemgaard et al., 2017);
6. B and T Lymphocyte Attenuator (BTLA; see US 2016/09222114); and
7. A2A adenosine receptor (A2AR; see Beavis et al., 2015; US 2013/0267515; US 2017/0166878; Leone et al., 2015; Mediavilla-Varela et al., 2017; Young et al., 2016).

Agents that reduce or block the activity of LAG-3 include, but are not limited to, BMS-986016, IMP321, and GSK2831781 (He et al., 2016).

Agents that reduce or block the activity of VISTA include, but are not limited to, small molecules, such as CA-170, and antibodies (e.g., Le Mercier et al., 2014).

Agents that reduce or block the activity of TIM-3 include, but are not limited to, antibodies such as MBG453 and TSR-022; see Dempke et al., 2017.

Agents that reduce or block the activity of KIRs include, but are not limited to, monoclonal antibodies such as IPH2101 and Lirilumab (BMS-986015, formerly IPH2102); see Benson & Caligiuri, 2014.

Agents that reduce or block the activity of IDO include, but are not limited to, epacadostat and agents disclosed in US 2017/0037125.

Agents that reduce or block the activity of BTLA include, but are not limited to, peptides (e.g., Spodzieja et al., 2017).

Agents that reduce or block the activity of A2AR include, but are not limited to, small molecules such as CPI-444 and vipadenant.

In some embodiments, the second therapy comprises a cytokine (e.g., interleukin 7).

In some embodiments, the second therapy comprises an agonist of a stimulatory checkpoint molecule. These molecules include, but are not limited to:

1. CD40;
2. OX40;
3. glucocorticoid-induced tumor necrosis factor-related protein (GITR); and
4. Inducible T-cell COStimulator (ICOS).

Agonists of CD40 include, but are not limited to, CD40 agonist monoclonal antibodies such as cp-870,893, ChiLob7/4, dacetuzumab, and lucatumumab. See, e.g., Vonderheide et al., 2007; Khubchandani et al., 2009; Johnson et al., 2010; Bensinger et al., 2012; Vonderheide and Glennie, 2013; Johnson et al., 2015.

Agonists of OX40 include, but are not limited to, OX40 agonist antibodies such as MOXR0916, MED16469, MED10562, PF-045618600, GSK3174998, and INCCAGN01949, and OX40L-Fc fusion proteins, such as MED16383. See, e.g., Huseni et al., 2014; Linch et al., 2015; Messenheimer et al., 2017. See also Shrimali et al., 2017.

Agonists of GITR include, but are not limited to, MEDI1873. See, e.g., Schaer et al., 2012; Tigue et al., 2017.

Agonists of ICOS include, but are not limited to, ICOS agonist antibodies JTX-2011 and GSK3359609. See, e.g., Harvey et al., 2015; Michaelson et al., 2016.

In other embodiments, the second therapy comprises a 4-1BB agonist (Shindo et al., 2015), such as urelumab; a 4-1BB antagonist (see US 2017/0174773); an inhibitor of anaplastic lymphoma kinase (ALK; Wang et al., 2014; US 2017/0274074), such as crizotinib, ceritinib, alectinib, PF-06463922, NVP-TAE684, AP26113, TSR-011, X-396, CEP-37440, RXDX-101; an inhibitor of histone deacetylase (HDAC; see US 2017/0327582); a VEGFR inhibitor, such as axitinib, sunitinib, sorafenib, tivozanib, bevacizumab; and/or an anti-CD27 antibody, such as varlilumab.

In some embodiments, the second therapy comprises a cancer vaccine (e.g., Duraiswamy et al., 2013). A "cancer vaccine" is an immunogenic composition intended to elicit an immune response against a particular antigen in the individual to which the cancer vaccine is administered. A cancer vaccine typically contains a tumor antigen which is able to induce or stimulate an immune response against the tumor antigen. A "tumor antigen" is an antigen that is present on the surface of a target tumor. A tumor antigen may be a molecule which is not expressed by a non-tumor cell or may be, for example, an altered version of a molecule expressed by a non-tumor cell (e.g., a protein that is misfolded, truncated, or otherwise mutated).

In some embodiments, the second therapy comprises a chimeric antigen receptor (CAR) T cell therapy. See, e.g., John et al., 2013; Chong et al., 2016.

In some embodiments, one or more of the peptides, modified peptides, nucleic acid molecules, CAR-T cells, and/or oncolytic viruses described above are administered in conjunction with a CAR-T cell cancer therapy to increase the efficacy of the CAR-T cell cancer therapy.

In some embodiments, one or more of the peptides, modified peptides, nucleic acid molecules, CAR-T cells, and/or oncolytic viruses described above are administered in conjunction with an oncolytic virus as disclosed, for example, in US 2017/0143780. Non-limiting examples of oncolytic viruses are described above.

Additional Therapeutic Uses

In some embodiments, one or more of the peptides, modified peptides, nucleic acid molecules, CAR-T cells, and/or oncolytic viruses described above are administered to a patient to treat infectious diseases, including chronic infections, caused, e.g., by viruses, fungi, bacteria, and protozoa, and helminths.

Examples of viral agents include human immunodeficiency virus (HIV), Epstein Barr Virus (EBV), *Herpes simplex* (HSV, including HSV1 and HSV2), Human Papillomavirus (HPV), Varicella zoster (VSV) Cytomegalovirus (CMV), and hepatitis A, B, and C viruses.

Examples of fungal agents include *Aspergillus, Candida, Coccidioides, Cryptococcus*, and *Histoplasma capsulatum.*

Examples of bacterial agents include Streptococcal bacteria (e.g., *pyogenes, agalactiae, pneumoniae*), *Chlamydia pneumoniae, Listeria monocytogenes*, and *Mycobacterium tuberculosis*.

Examples of protozoa include Sarcodina (e.g., *Entamoeba*), Mastigophora (e.g., Giardia), Ciliophora (e.g., *Balantidium*), and Sporozoa (e.g., *Plasmodium falciparum, Cryptosporidium*).

Examples of helminths include Platyhelminths (e.g., trematodes, cestodes), Acanthocephalins, and Nematodes.

In some embodiments, one or more of the peptides, modified peptides, nucleic acid molecules, CAR-T cells, and/or oncolytic viruses described above are administered as a vaccine adjuvant, to enhance a response to vaccination (e.g., by increasing effector T cells and/or reducing T cell exhaustion). The vaccine can be, for example, an RNA vaccine (e.g., US 2016/0130345, US 2017/0182150), a DNA vaccine, a recombinant vector, a protein vaccine, or a peptide vaccine. Such vaccines can be delivered, for example, using virus-like particles, as is well known in the art.

In some embodiments, one or more of the peptides, modified peptides, nucleic acid molecules, CAR-T cells, and/or oncolytic viruses described above are administered to treat sepsis.

In some embodiments, one or more of the peptides, modified peptides, nucleic acid molecules, CAR-T cells, and/or oncolytic viruses described above are administered to promote hair color re-pigmentation. In some embodiments, one or more of the peptides, modified peptides, nucleic acid molecules, CAR-T cells, and/or oncolytic viruses described herein are administered to promote lightening of pigmented skin lesions.

Example 1. Peptide L D01 Binds to Human and Mouse PD-1

BIACORE® assays were carried out using a BIACORE® T-200 at 25° C. The assay and regeneration buffers contained 10 mM HEPES (pH 7.4), 150 mM NaCl, 3 mM EDTA, and 0.05% P20. The immobilization buffer was 10 mM sodium acetate, pH 5.0. The flow rate used for immobilizing the ligand was 5 μl/min. The flow rate for kinetics analysis was 30 μl/min.

Scouting. 4400 RU of peptide LD01 was directly immobilized on flow cell 2 of the CM5 chip by amine coupling method (EDC/NHS). The un-occupied sites were blocked with 1M ethanol amine. Scouting was performed at a single analyte concentration of 290 nM to confirm yes/no binding. Flow cell 1 was kept blank and used for reference subtraction. Binding of analyte to the ligand was monitored in real time.

Full Kinetics. Based on the scouting results, full kinetics was performed at analyte concentration of 100 nM, followed by serial dilution to 50, 25, 12.5, 6.25, 3.125, 1.562 and 0 nM concentration or as indicated. $K_D$ was determined from the observed $k_{on}$ (on rate) and $k_{off}$ (off rate) or by steady state equilibrium kinetics for the interactions with fast off rate.

Chi square ($\chi^2$) analysis was carried out between the actual Sensorgram and the sensorgram generated from the BIAnalysis software to determine the accuracy of the analysis. $\chi^2$ value within 1-2 is considered significant (accurate) and below 1 is highly significant (highly accurate).

Figure 2:
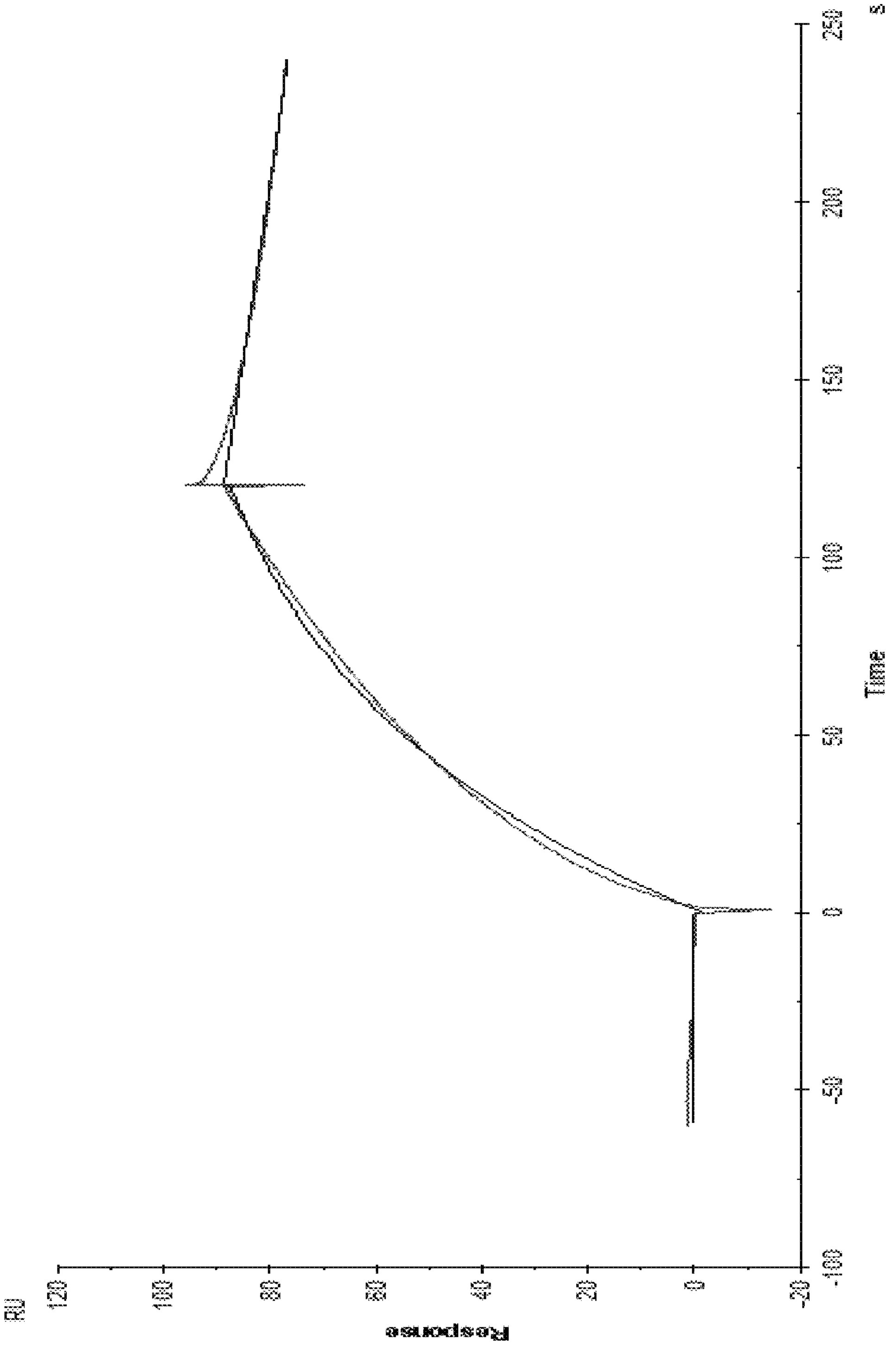
FIG. 2 is a graph providing single concentration BIACORE® data for peptide LD01 binding to mouse PD-1.
Figure 3:
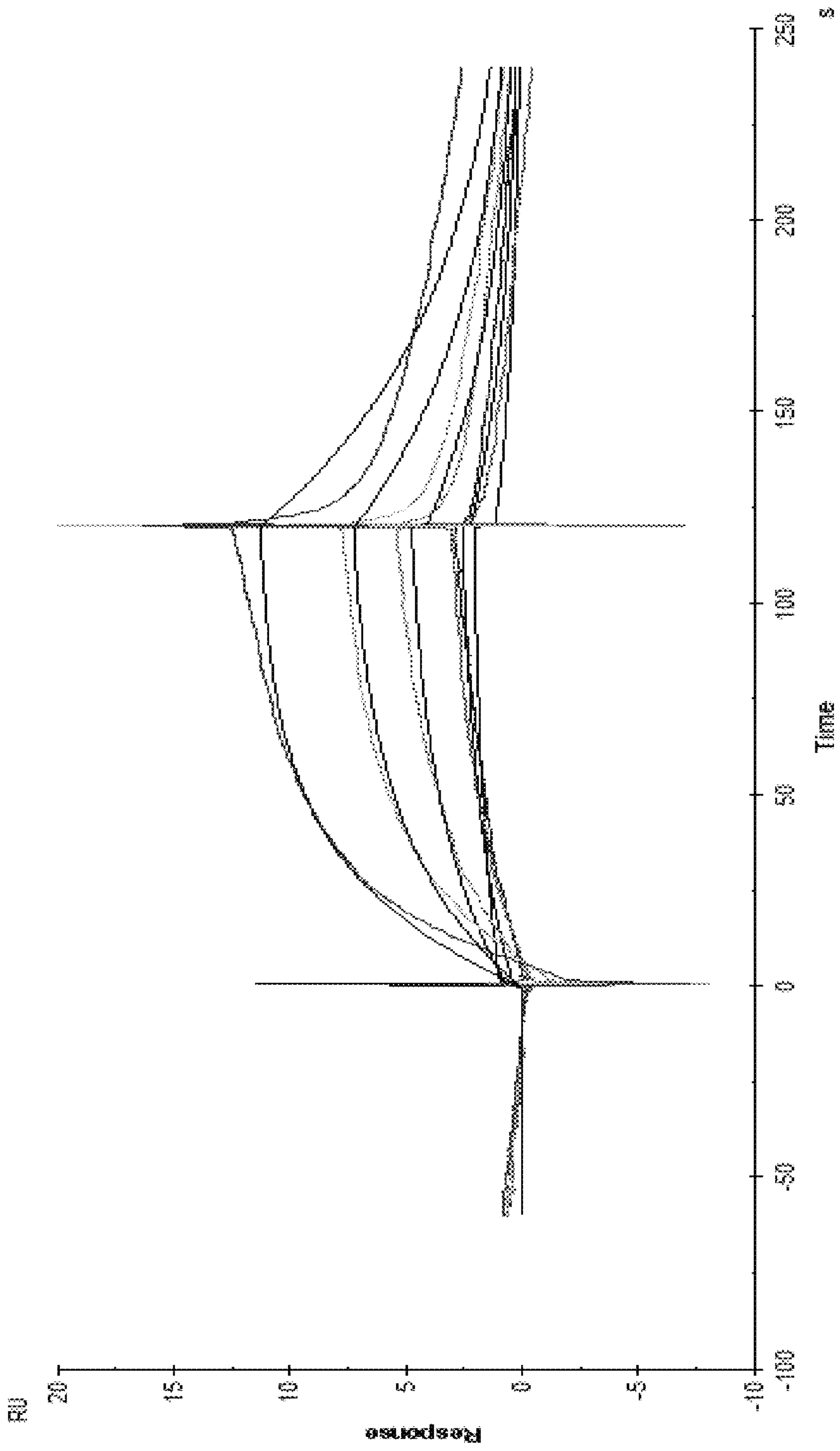
FIG. 3 is a graph showing kinetics of peptide LD01 binding to mouse PD-1.

The single concentration binding data are shown in FIG. 1 and FIG. 2 for the human and mouse PD1, respectively. The kinetic data for binding to mouse PD-1 are shown in FIG. 3. These data demonstrate that peptide LD01 binds to both human and mouse PD-1 and support the use of mouse models in the examples below.

Example 2. Peptide LD01 Enhances Binding of a Human PD-L1-Fc Fusion Protein to Human PD-1 Expressed on the Surface of Jurkat Cells A human T cell line (Jurkat) stably expressing human PD-1 on its surface was purchased from Promega. This cell line was cultured using sterile techniques and maintained in log-phase growth. PD-1 protein expression levels were measured using an anti-human PD-1 antibody labeled with allophycocyanin (APC) for quality assessment.

For the experiment, 200 μL of 2.5*10^5 cells were plated in staining buffer into a microtiter plate. These cells were incubated with varying concentrations of peptide LD01 in staining buffer for 1 hour, washed, and then incubated with PD-L1-Fc fusion protein for 1 hour. After another wash step, the cells were incubated with anti-human Fc labeled with AF647 for 30 minutes. After several washes, the mean fluorescence intensity due to PD-L1-Fc binding to PD-1 was measured by flow cytometry.

Figure 4A:
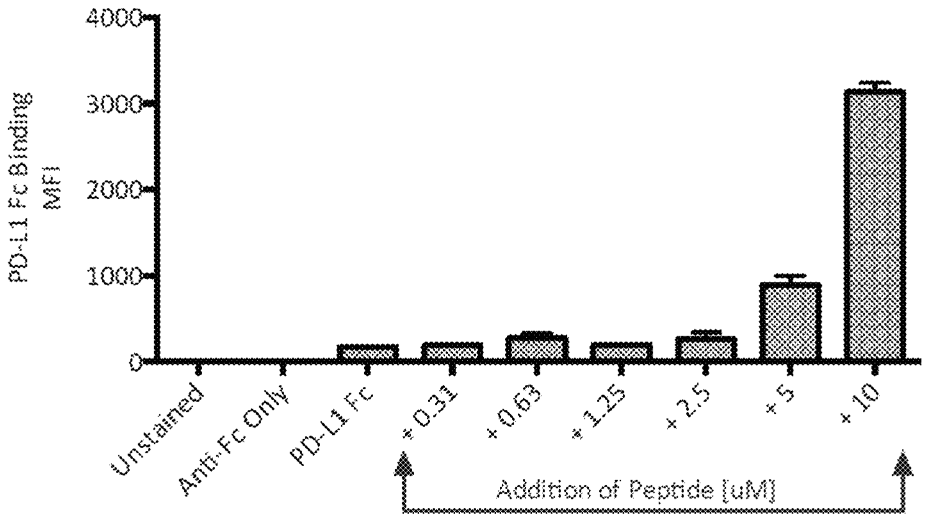
FIGS. 4A-C are graphs showing the effects of peptides on the binding of PD-L1-Fc fusion protein to cell surface-expressed human PD-1.
Figure 4B:
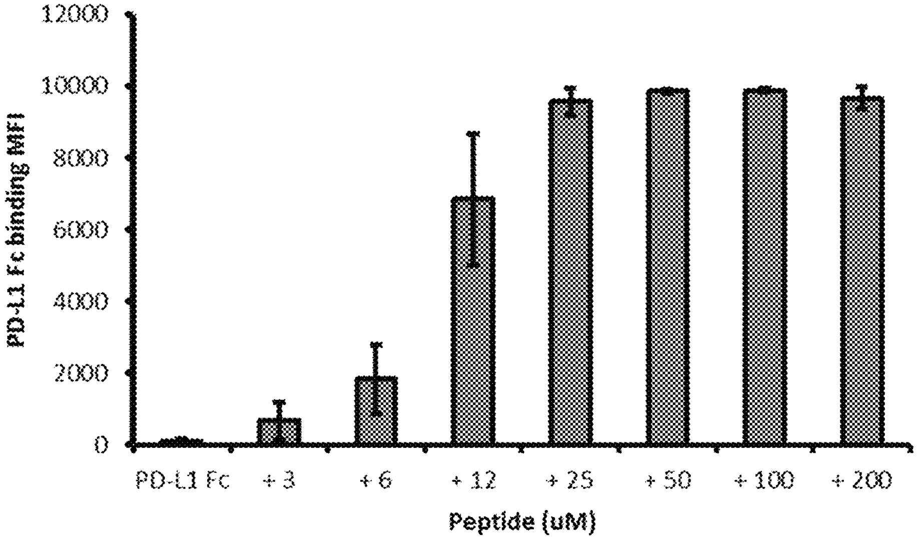
Figure 4C:
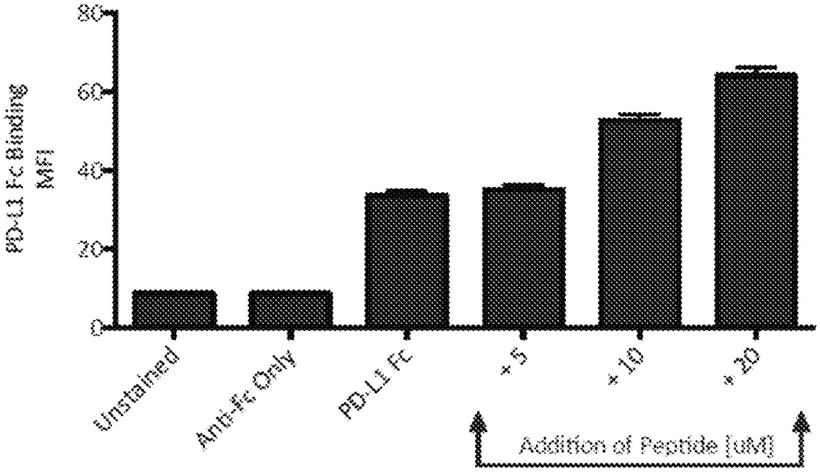

The results are shown in FIGS. 4A-C. These results demonstrate that peptide LD01 enhances binding of the human PD-L1-Fc fusion protein to human PD-1-expressing Jurkat cells with an increasing dose-response trend.

Example 3. Peptide LD01 Enhances Binding of PD-L1 Fc to PD-1 in a Cell-Free Assay Microtiter plates were coated with peptide LD01 at 4° C. overnight. The plates were washed and blocked with 1% BSA for 1 hour at room temperature. The plates were then incubated with 100 μL of 1 μg/mL PD-1 at room temperature for 1 hour. The plates were again washed and incubated with PD-L1 at room temperature for 1 hour. After another round of washes, the plates were incubated with anti-human IgG-HRP. After incubation for 1 hour and washes, the HRP was detected by incubating with TMB substrate, and the OD were read on a microplate reader.

Figure 5:
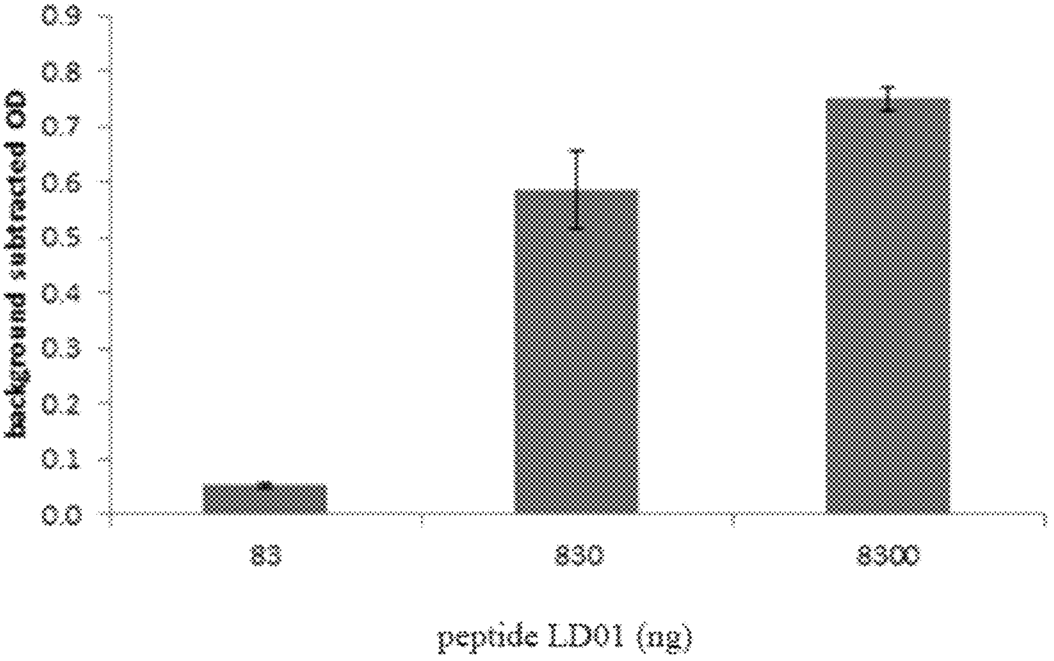
FIG. 5 is a graph showing effect of peptide LD01 on the binding of PD-L1-Fc fusion protein to PD-1 in a cell-free assay.

The results are shown in FIG. 5. These results confirm that peptide LD01 enhances binding of the human PD-L1-Fc fusion protein to human PD-1 in a cell-free assay.

Example 4. Effect of Peptide LD01 on Mouse Splenocyte Proliferation

PD-L1-Fc fusion protein is hypothesized to reduce anti-CD3 induced splenocyte proliferation. An experiment was carried out to determine whether the effect of peptide LD01 on PD-L1-Fc-mediated proliferation.

Carboxyfluorescein diacetate succinimidyl ester (CFSE)-labeled mouse splenocytes (400,000 cells, 5 μM CFSE) were stimulated using 1 μg/mL anti-CD3 antibody and varying levels of PD-L1-Fc or an irrelevant control Fc. To monitor the effect of peptide LD01 on PD-1, varying concentrations of peptide LD01 (1 μM, 5 μM, and 25 μM) were tested for their effect on the proliferation of the splenocytes. The CFSE dilution profiles were analyzed by flow cytometry after 3 days of treatment.

Figure 6:
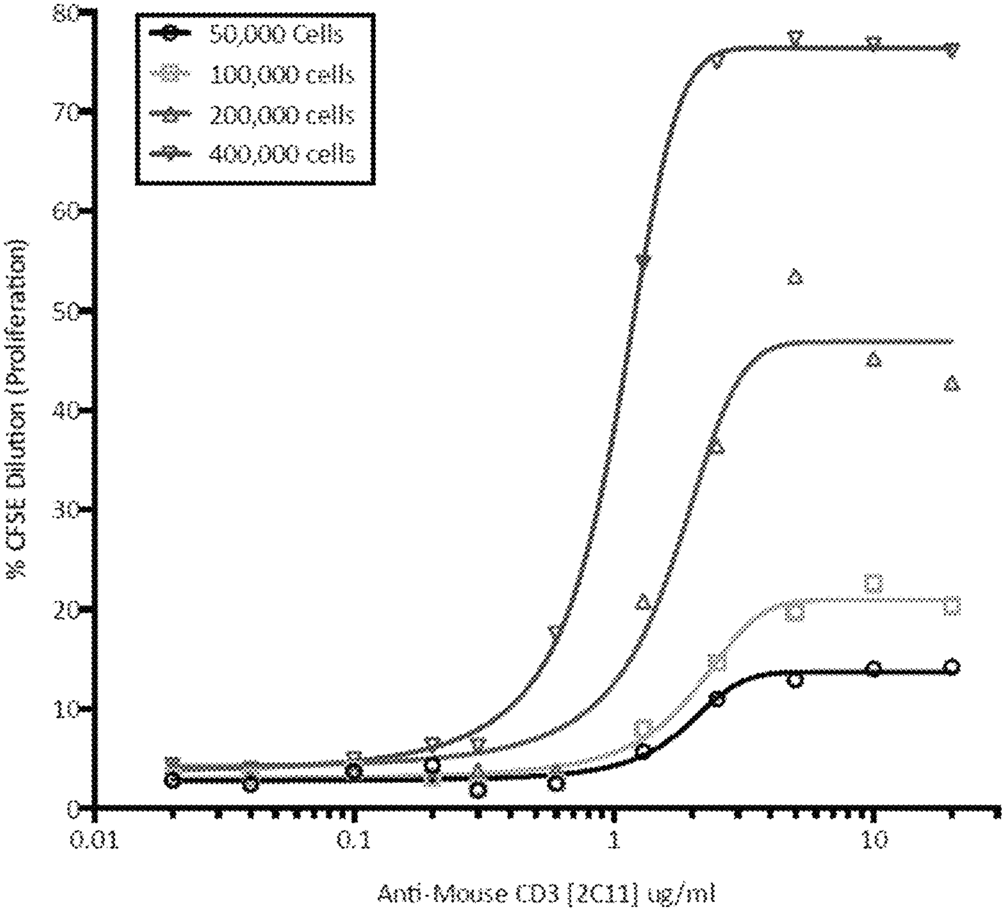
FIG. 6 is a graph showing splenocyte proliferation as a function of anti-CD3 antibody concentration.
Figure 7:
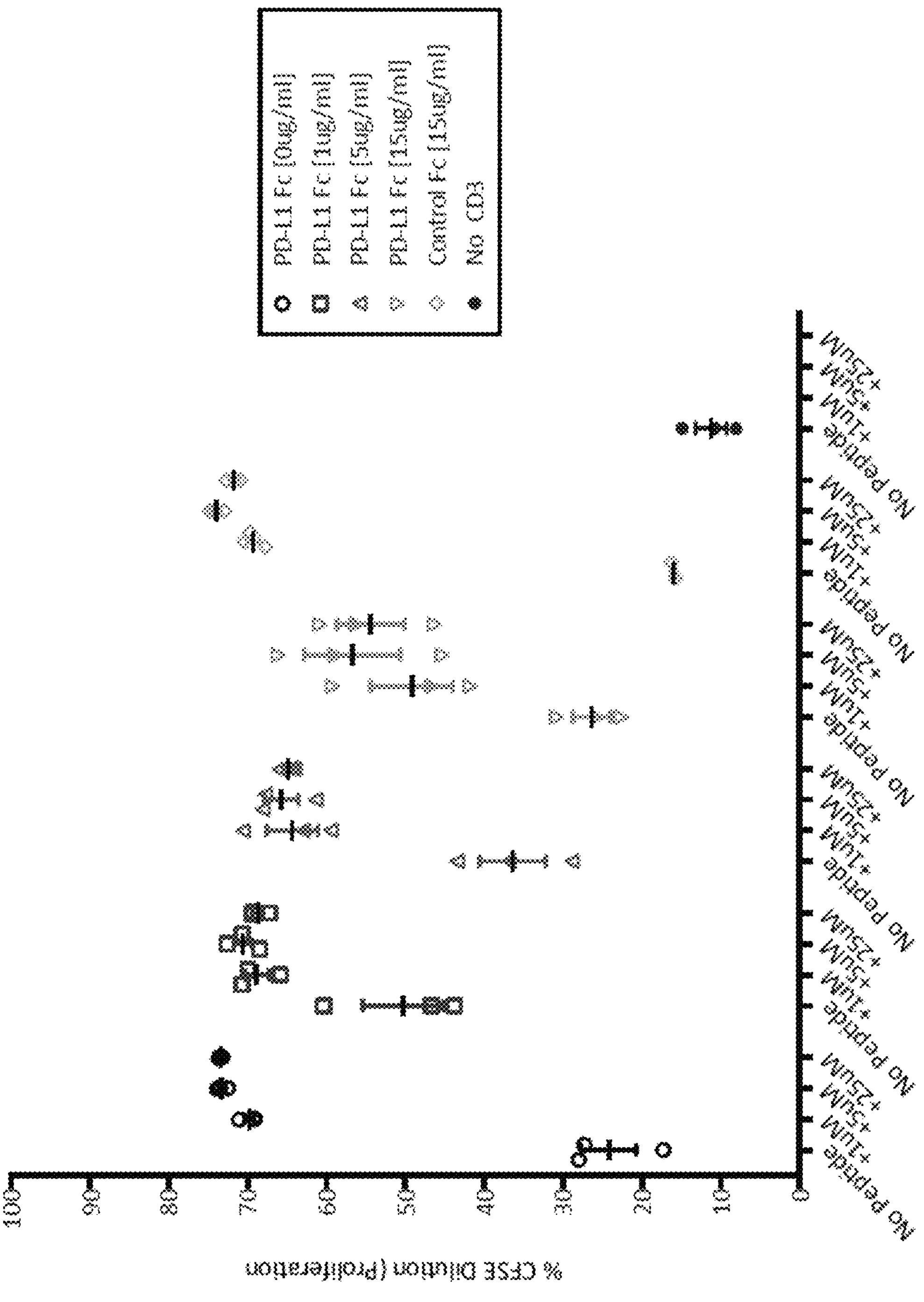
FIG. 7 is a graph showing that peptide LD01 enhances proliferation of anti-CD3-stimulated splenocyte proliferation in the presence and absence of exogenously added PD-L1-Fc fusion protein.

Titration results of cell numbers and anti-CD3 antibody concentration are shown in FIG. 6, and the peptide LD01 data is shown in FIG. 7. These results demonstrate that peptide LD01 enhances proliferation of anti-CD3 stimulated mouse splenocytes in the presence and absence of exogenously added PD-L1-Fc.

Example 5. Effect of Peptide LD01 in a Mouse Melanoma Model

To assess the in vivo functionality of peptide LD01, anti-metastasis activity was evaluated in a syngeneic model of B16-F-10 mouse melanoma in immunocompetent C57/BL6 mice. In brief, murine B16-F10-LacZ cells obtained from ATCC were cultured in RPMI-1640 media supplemented with 10% FBS. Once confluent, cells were collected, and $2\times10^5$ cells in 200 µl of PBS were injected into each mouse intravenously via the tail vein. After cells were delivered, animals were assigned randomly to the study cohorts (5 mice in each group). Test sample, route of treatment and treatment days are detailed in Table TA. Because the in vivo half-life of peptides is relatively short (hours) compared to antibodies (weeks), peptides were delivered intravenously and given more frequently.

TABLE 1A

| Cohort | Test sample | Route | Treatment days |
|---|---|---|---|
| 1 | No treatment | | |
| 2 | MOG control peptide (200 µg) | i.v. | 1, 2, 4, 6, 8, 12 |
| 3 | peptide LD01 (20 µg) | i.v. | 1, 2, 4, 6, 8, 12 |
| 4 | peptide LD01 (200 µg) | i.v. | 1, 2, 4, 6, 8, 12 |
| 5 | Anti-PD-L1 antibody (200 µg) | i.p. | 2, 5, 7, 9, 12 |
| 6 | Anti-PD1 antibody (200 µg) | i.p. | 2, 5, 7, 9, 12 |

The negative control peptide used in this study was the myelin oligodendrocyte glycoprotein (MOG) peptide (MEVGWYRSPFSRVVHLYRNGK, SEQ ID NO:33). 200 µg of peptide or antibody was administered per treatment day. At day 14 post cell injection, the mice were euthanized, lungs removed and fixed in Fekete's solution. The tumor nodules were counted.

Figure 8:
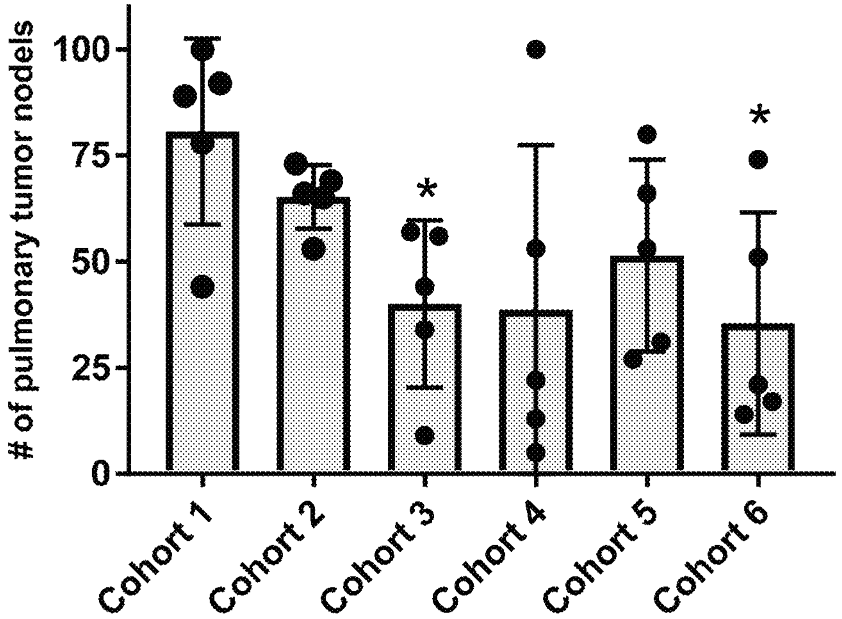
FIG. 8 is a graph showing the effect of peptide LD01 on the number of pulmonary tumor nodules in a mouse melanoma model. * $p<0.05$.
Figure 9:
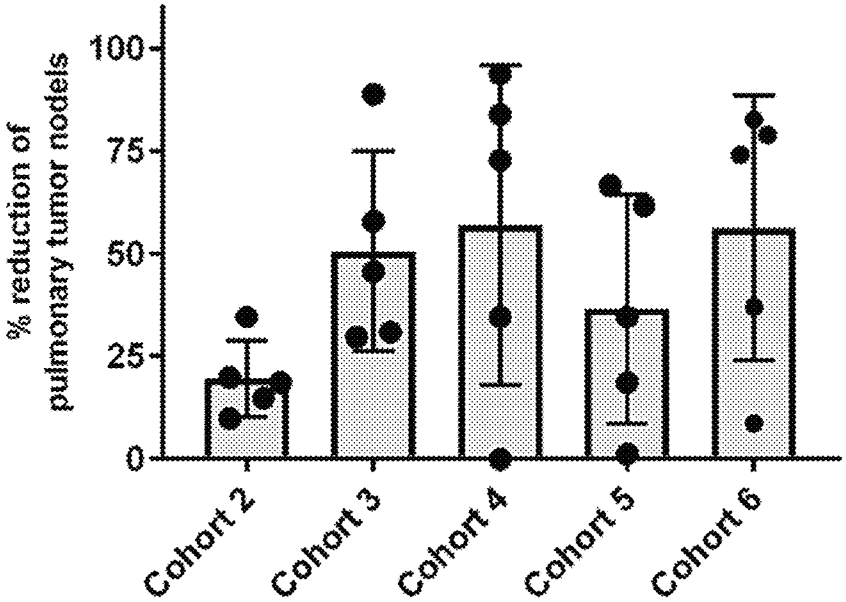
FIG. 9 is a graph showing the percent reduction in pulmonary tumor nodules by peptide LD01 in a mouse melanoma model.
Figure 10:
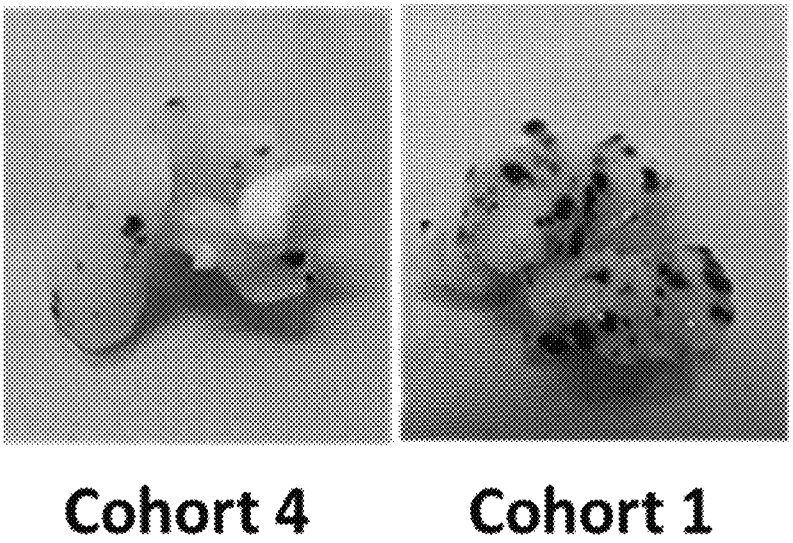
FIG. 10 compares the effect of peptide LD01 on pulmonary tumor nodules in a mouse melanoma model as described in Example 5. Left (Cohort 4), treatment with 200 μg peptide LD01. Right (Cohort 1), no treatment.

The number of tumor nodules for individual mice are shown in FIG. 8, while percentage reduction of tumor nodules in each cohort relative to no treatment (Cohort 1) is shown in FIG. 9. Significant differences between the no treatment (Cohort 1) and peptide LD01 (Cohort 3) or anti-PD-1 antibody (Cohort 6) were detected using the unpaired t-test and denoted by * $p<0.05$ in FIG. 8. Examples of macroscopic lung images for the no treatment (Cohort 1) and peptide LD01 (Cohort 4) are shown in FIG. 10. These results demonstrate that peptide LD01 (Cohorts 3 and 4) is functionally active in vivo, reducing lung metastasis by ~50% relative to no treatment (Cohort 1). Moreover, peptide LD01 (Cohorts 3 and 4) efficacy was similar to or slightly above treatment with anti-PD-L1 or anti-PD-1 antibodies (Cohorts 5 and 6).

Peptides LD01, LD10da, and LD16da were tested as described above, this time using peptide LD12 (cohort 2) as the negative control. Test sample, route of treatment and treatment days are detailed in Table IB.

TABLE 1B

| Cohort | Test sample | Route | Treatment days |
|---|---|---|---|
| 1 | Saline; No treatment | | |
| 2 | +LD12 | i.v. | 1, 2, 4, 6, 8, 12 |
| 3 | +LD01 | i.v. | 1, 2, 4, 6, 8, 12 |
| 4 | +LD10da | i.v. | 1, 2, 4, 6, 8, 12 |
| 5 | +LD16da | i.v. | 1, 2, 4, 6, 8, 12 |
| 6 | α-PD1 mAb | i.v. | 1, 2, 4, 6, 8, 12 |

Figure 11:
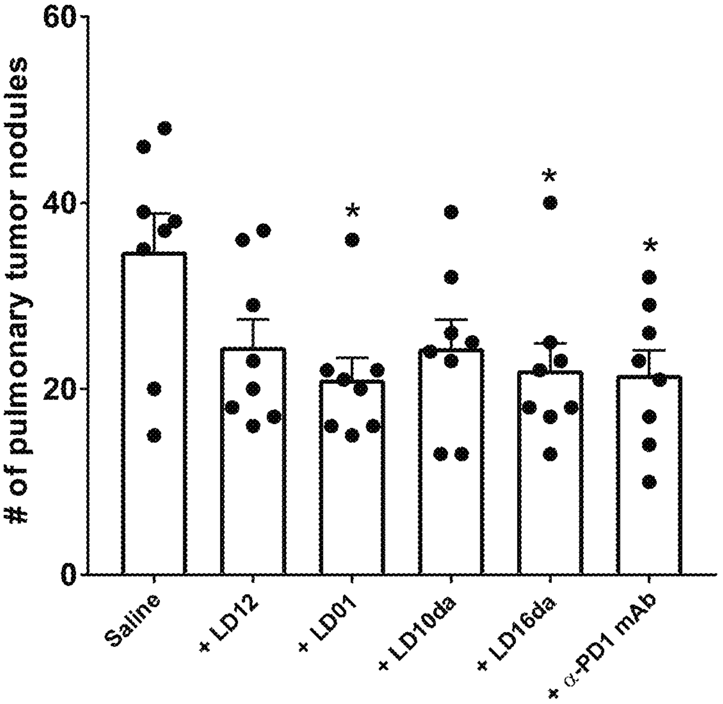
FIG. 11 is a graph showing the effect of peptides LD12, LD01, LD10da, and LD16da on the number of pulmonary tumor nodules in a mouse melanoma model. * $p<0.05$.

The number of tumor nodules for individual mice are shown in FIG. 11. Significant differences between the no treatment saline (Cohort 1) and LD01 (Cohort 3), LD16da (Cohort 5) or α-PD-1 mAb (Cohort 6) were detected using the one-way ANOVA test (* $p<0.05$) in FIG. 11. These results demonstrate that LD01 (Cohort 3) and LD16da (Cohort 5) are functionally active in vivo, reducing lung metastasis by ~30% relative to no treatment saline (Cohort 1).

Example 6. Effect of Peptide LD01 on the Immunogenicity of a Malaria Vaccine

The effect of peptide LD01 on the immunogenicity of a malaria vaccines was evaluated in immunocompetent Balb/c mice. Balb/c mice were immunized intramuscularly with $10^{10}$ virus particles of a recombinant replication defective adenovirus expressing the *Plasmodium yoelli* circumsporozoite protein (AdPyCSP). Test sample, number of mice, route of treatment, and treatment days are shown in Table 2A.

TABLE 2A

| Cohort | Test Sample | # Mice | Route | Treatment days |
|---|---|---|---|---|
| 1 | AdPyCSP only | 5 | — | — |
| 2 | AdPyCSP + control OVA peptide (200 µg) | 5 | i.p. | 0, 1, 3, 5, 7 |
| 3 | AdPyCSP + peptide LD01 (200 µg) | 5 | i.p. | 0, 1, 3, 5, 7 |
| 4 | AdPyCSP + anti-PD1 antibody (200 µg) | 5 | i.p. | 0, 1, 3, 5, 7 |
| 5 | AdPyCSP + anti-PDL1 antibody (200 µg) | 5 | i.p. | 0, 1, 3, 5, 7 |

The negative control peptide used in this study was the ovalbumin (OVA) peptide (SIINFEKL, SEQ ID NO:34). At day 12 post immunization, mice were euthanized, individual spleens removed, and the number of splenic CSP-specific, IFNγ-secreting $CD8^+$ T cells were determined by ELISPOT assay. For the ELISPOT assay splenocytes were stimulated with the peptide SYVPSAEQI (SEQ ID NO:35), an H-2Kd-restricted $CD8^+$ T cell epitope of PyCSP.

Figure 12:
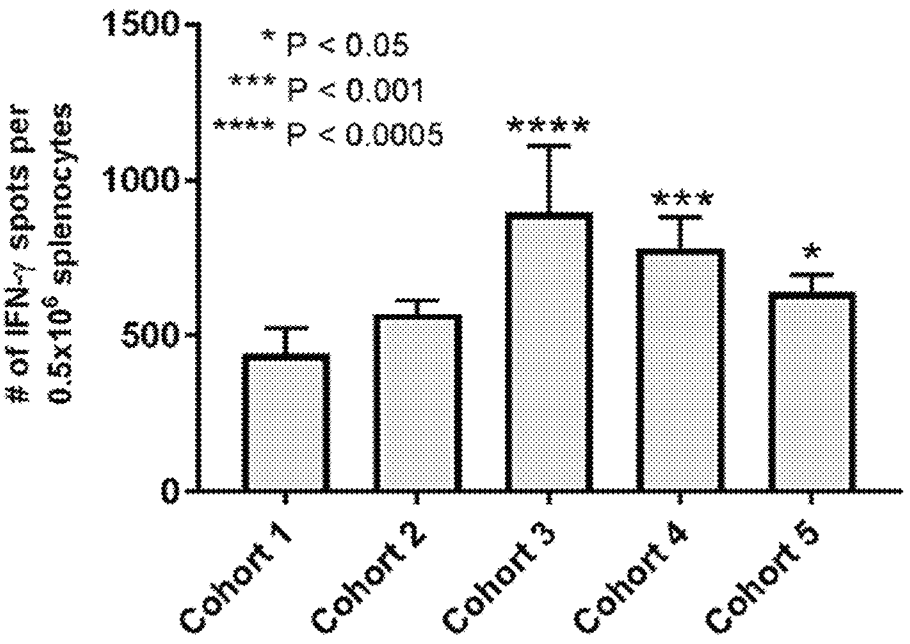
FIG. 12 is a graph showing the effect of peptide LD01 on the immunogenicity of a malaria vaccine (Example 6).

Shown in FIG. 12 is the average number±standard deviation of CSP-specific, IFNγ-secreting CD8 T cells per $0.5\times10^6$ splenocytes for each cohort. Significant differences between the AdPyCSP alone (Cohort 1) and peptide LD01 (Cohort 3), anti-PD-1 antibody (Cohort 4) or anti-PD-L1 antibody (Cohort 5) were detected using the one-way ANOVA test (** $p<0.0005$, * $p<0.001$, and * $p<0.05$). These results further demonstrate that peptide LD01 (Cohort 3) is functionally active in vivo, increasing the number of CSP-specific, IFNγ-secreting CD8 T cells ~2-fold relative to AdPyCSP alone (Cohort 1). Moreover, peptide LD01 (Cohort 3) immunogenicity was slightly above treatment with anti-PD-1 or -PD-L1 antibody (Cohort 4 and 5).

Peptides LD01, LD10da, and LD16da were tested as described above, this time using peptide LD12 (cohort 2) as the negative control. Test sample, route of treatment and treatment days are detailed in Table 2B.

TABLE 2B

| Cohort | Test Sample | # Mice | Route | Treatment days |
|---|---|---|---|---|
| 1 | AdPyCSP only | 5 | — | — |
| 2 | AdPyCSP + LD12 (200 µg) | 5 | i.p. | 0, 1, 3, 5, 7 |
| 3 | AdPyCSP + LD01 (200 µg) | 5 | i.p. | 0, 1, 3, 5, 7 |

TABLE 2B-continued

| Cohort | Test Sample | # Mice | Route | Treatment days |
|---|---|---|---|---|
| 4 | AdPyCSP + LD10da (200 μg) | 5 | i.p. | 0, 1, 3, 5, 7 |
| 5 | AdPyCSP + LD16da (200 μg) | 5 | i.p. | 0, 1, 3, 5, 7 |
| 6 | AdPyCSP + α-PD1 mAb (200 μg) | 5 | i.p. | 0, 1, 3, 5, 7 |

At day 12 post immunization, mice were euthanized, individual spleens removed, and the number of splenic CSP-specific, IFNγ-secreting $CD8^+$ T cells were determined by ELISPOT assay. For the ELISPOT assay splenocytes were stimulated with the peptide SYVPSAEQI (SEQ ID NO:35), an H-2Kd-restricted $CD8^+$ T cell epitope of PyCSP.

Figure 13:
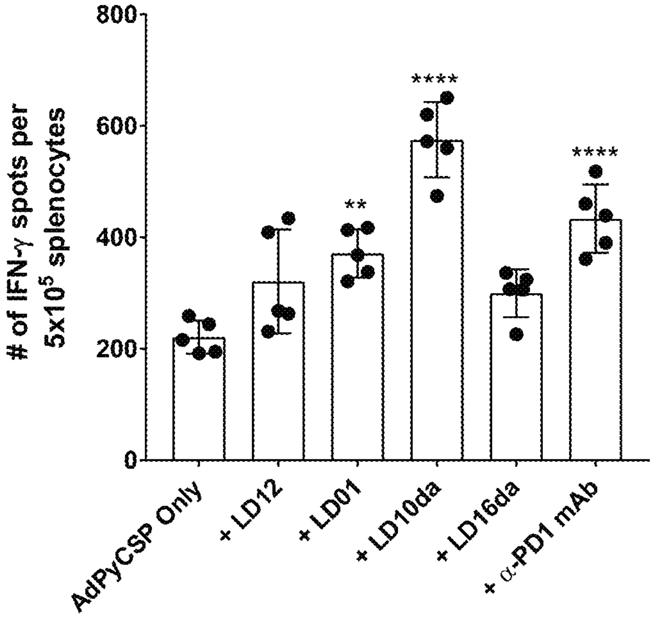
FIG. 13 is a graph showing the effect of peptides LD12, LD01, LD10da, and LD16da on the immunogenicity of a malaria vaccine (Example 6).

Shown in FIG. 13 is the average number±standard deviation of CSP-specific, IFNγ-secreting $CD8^+$ T cells per $5\times10^5$ splenocytes for each cohort. Significant differences relative to AdPyCSP alone were detected using the one-way ANOVA test (** $p<0.0001$,  $p<0.005$). These results further demonstrate that LD01 (Cohort 3) and LD10da (Cohort 4) are functionally active in vivo, increasing the number of CSP-specific, IFNγ-secreting CD8 T cells ~1.5 to 2.5-fold, respectively, relative to AdPyCSP alone (Cohort 1). Moreover, LD10da (Cohort 4) immunogenicity was slightly above treatment with α-PD-1 mAb (Cohort 6).

Example 7. Effect of Peptide LD01 in a Mouse Sepsis Model

The effect of peptide LD01 was studied in a representative, clinically relevant model of sepsis, i.e., CD1 mice with intra-abdominal peritonitis induced by cecal ligation and puncture (CLP).

CD1 mice were anesthetized, a midline abdominal incision made, the cecum was ligated and punctured, and then the incision closed. 200 μg of peptide LD01 or a control peptide (SEQ ID NO:2) was administered intraperitoneally at 6, 24, and 48 hours after surgery. Administration of peptide LD01 conferred a survival advantage with the peptide LD01 cohort having a survival rate greater than double than the survival of the control peptide, 70% (7/10) versus 30% (3/10), respectively.

Figure 14:
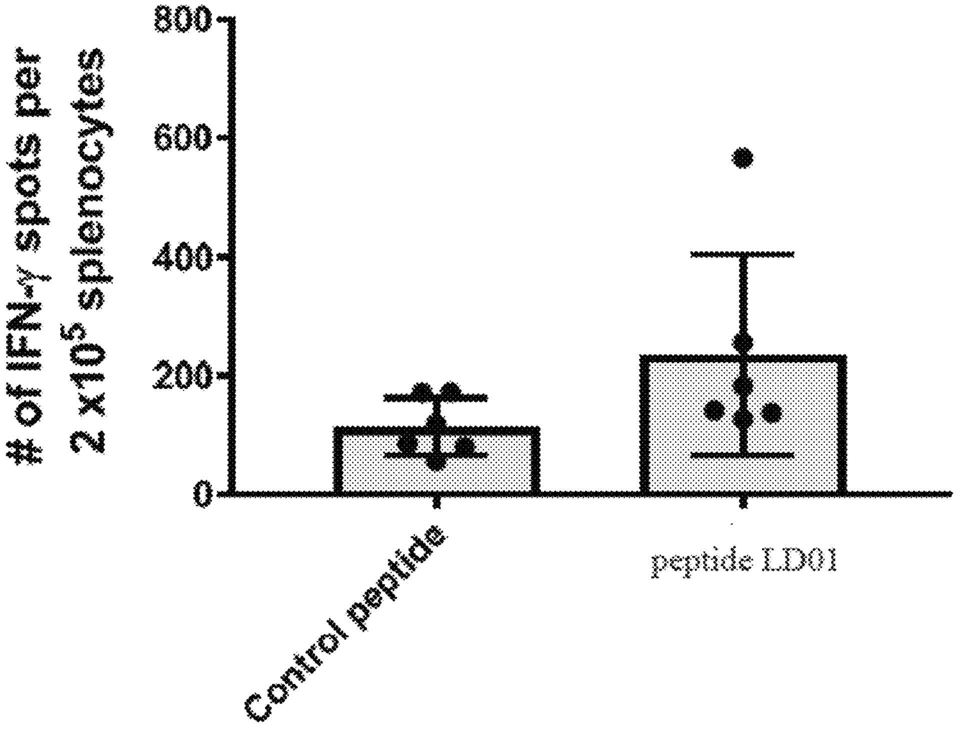
FIG. 14 is a graph showing the effect of peptide LD01 on the number of IFNγ-secreting T cells per $2\times10^5$ splenocytes in a mouse sepsis model.

In a separate study, the effect of peptide LD01 on augmenting IFNγ production by T cells during sepsis was assessed. Following CLP surgery, mice were treated at 6, 24, 48, 72 and 96 hours with peptide LD01 or the control peptide. Twenty-four hours later, mice were euthanized, individual spleens were removed, and the number of splenic IFNγ-secreting T cells were determined by ELISPOT assay. For the ELISPOT assay splenocytes were stimulated via anti-CD3 and anti-CD28. Shown in FIG. 14 is the number of IFNγ-secreting T cells per $2\times10^5$ splenocytes. Peptide LD01 treatment caused an increase in the number of IFNγ-secreting T cells relative to the control peptide, which supports the utility of peptide LD01 in reversing the sepsis-induced defect in IFNγ secretion by T cells.

Example 8. PATHHUNTER© Checkpoint Signaling Assays

Peptides were tested for their ability to inhibit the binding of PD-L1 to PD-1 or CD86 to CTLA-4 using PATHHUNTER© checkpoint signaling assays (DiscoverX).

PATHHUNTER©PD-1 and PD-L1 and CTLA4 and CD86 cell lines were expanded from freezer stocks according to standard procedures. PD-1 cells were pre-incubated with peptides, followed by incubation with PD-L1 cells. PD-1 Jurkat cells (20,000 cells per well) were seeded in a total volume of 50 μL into white-walled, 96-well microplates in assay buffer. Serial Dilution of peptide stocks was performed to generate 11× sample in assay buffer. 10 μL of 11× sample was added to PD-1 cells and incubated at 37° C. for 60 minutes. 50 μL U-2 OS PD-L1 cells (30,000 cells per well in assay buffer) were added, and the cells were co-cultured at room temperature for 2 hours. Similarly, CTLA4 cells were pre-incubated with peptides, followed by incubation with CD86 cells. CTLA4 Jurkat cells (20,000 cells per well) were seeded in a total volume of 50 μL into white-walled, 96-well microplates in assay buffer. Serial dilution of peptide stocks was performed to generate 11× sample in assay buffer. 10 μL of 11× sample was added to CTLA4 cells and incubated at 37° C. for 60 minutes. 50 μL U-2 OS CD86 cells (30,000 cells per well in assay buffer) were added, and the cells were co-cultured at room temperature for 4 hours.

Compound activity was analyzed using CBIS data analysis suite (ChemInnovation, CA). The results are shown in Tables 3 and 4. For antagonist mode assays, percentage inhibition efficacy was calculated using the following formula, in which RLU means relative light units:

$$100\times[1-\left[\frac{(\text{mean } RLU \text{ of test sample})-(\text{mean } RLU \text{ of vehicle control})}{(\text{mean } RLU \text{ of } EC_{80} \text{ control})-(\text{mean } RLU \text{ of vehicle control})}\right]]$$

The tested peptides exhibited a wide range of inhibition efficacy in the PD-1 as well as the CTLA-4 PATHHUNTER® assays as shown in Tables 3 and 4. Surprisingly, many of the peptides showed high efficacy in both assays, indicating their dual specificity for PD-1 and CTLA-4.

TABLE 3

Effect of Peptides on the Binding of PD-L1 to PD-1

| SEQ ID NO: | peptide | conc. (μM) | % inhibition Study 1 | Study 2 | Study 4 | Study 5 | Study 6 |
|---|---|---|---|---|---|---|---|
| 1 | LD01 | 100 | 50.5 | 79 | 65 | 24 | 83 |
| 2 | LD02 | 100 | 7 | 10 | | | |
| 3 | LD12 | 100 | 14 | 5 | | 18 | 4 |
| 4 | LD12a | 100 | | | | 18.5 | |
| 5 | LD11 | 100 | 44 | 59 | | | |
| 6 | LD03 | 100 | | | | 0 | |
| 7 | LD04 | 100 | | | | 87 | |
| 8 | LD40 | 100 | | | | 80 | |
| 9 | LD41 | 100 | | | | | 1.4 |
| 10 | LD42 | 100 | | | | | 0.8 |
| 11 | LD01r | 125 | | 74 | 66 | | |
| 12 | LD10 | 106 | 79 | 80 | 92 | | 86 |
| 13 | LD10 Q4A | 100 | | | | | 3 |
| 14 | LD10 T7A | 100 | | | | | 1 |
| 15 | LD10 R9A | 100 | | | | | 53 |
| 16 | LD10 N11A | 100 | | | | | 2 |
| 17 | LD10 P15A | 100 | | | | | 35 |
| 18 | LD10 L8A | 100 | | | | | 6 |
| 19 | LD10 L16A | 100 | | | | | 6 |
| 20 | LD10 T13A | 100 | | | | | 4 |
| 21 | LD17 | 100 | | 90 | | 94.5 | |
| 22 | LD17m | 100 | | | | 78 | |
| 23 | LD10aa | 50 | | | 10 | | |
| 24 | LD10da | 100 | | | 91 | | 26 |
| 25 | LD10da m | 100 | | | | | 2 |
| 26 | LD16 | 100 | | 90 | | | 0 |
| 27 | LD01 TQ19 | 100 | | | 93 | 22 | |

TABLE 3-continued

| Effect of Peptides on the Binding of PD-L1 to PD-1 | | | | | | | |
|---|---|---|---|---|---|---|---|
| SEQ | | | % inhibition | | | | |
| ID NO: | peptide | conc. (μM) | Study 1 | Study 2 | Study 4 | Study 5 | Study 6 |
| 28 | LD16m | 100 | | | | 15 | |
| 29 | LD01 TQ19 aa | 100 | | | 91 | | |
| 30 | LD01 TQ19 da/ LD16 da | 100 | | | 96 | | 1 |
| 31 | LD01 TQ19 da m | 100 | | | | | 6 |
| 32 | LD05 | 100 | 18 | | | | |

TABLE 4

| Effect of Peptides on the Binding of CD86 to CTLA-4 | | | | | | | |
|---|---|---|---|---|---|---|---|
| SEQ | | | % inhibition | | | | |
| ID NO: | peptide | conc. (μM) | Study 1 | Study 2 | Study 4 | Study 5 | Study 6 |
| 1 | LD01 | 100 | | 51 | 16 | 21 | 46 |
| 2 | LD02 | 100 | | −1 | 0 | | |
| 3 | LD12 | 100 | | −10 | −7 | 8 | −10 |
| 4 | LD12a | 100 | | | | 6 | |
| 5 | LD11 | 100 | | 28 | | | |
| 6 | LD03 | 100 | | | | −9 | |
| 7 | LD04 | 100 | | | | 76.5 | |
| 8 | LD40 | 100 | | | | 81.5 | |
| 9 | LD41 | 100 | | | | | −9 |
| 10 | LD42 | 100 | | | | | −4 |
| 11 | LD01r | 125 | | | 77 | | |
| 12 | LD10 | 106 | | 88 | 95 | | 95 |
| 13 | LD10 Q4A | 100 | | | | | −16.5 |
| 14 | LD10 T7A | 100 | | | | | −17 |
| 15 | LD10 R9A | 100 | | | | | 49.5 |
| 16 | LD10 N11A | 100 | | | | | −17 |
| 17 | LD10 P15A | 100 | | | | | 13 |
| 18 | LD10 L8A | 100 | | | | | −11.5 |
| 19 | LD10 L16A | 100 | | | | | −3 |
| 20 | LD10 T13A | 100 | | | | | −7 |
| 21 | LD17 | 100 | | | | 102 | |
| 22 | LD17m | 100 | | | | 82 | |
| 23 | LD10aa | 50 | | | 18 | | |
| 24 | LD10da | 100 | | | 98 | | 22 |
| 25 | LD10da m | 100 | | | | | −12 |
| 26 | LD16 | 100 | | | | | 0 |
| 27 | LD01 TQ19 | 100 | | | 91 | 18 | |
| 28 | LD16m | 100 | | | | 17 | |
| 29 | LD01 TQ19 aa | 100 | | | 96 | | |
| 30 | LD01 TQ19 da/LD16 da | 100 | | | 99 | | −54 |
| 31 | LD01 TQ19 da m | 100 | | | | | −2 |

Example 9. Effect of LD01 on the IFN-γ Secretion by Human PBMCs

Figure 15:
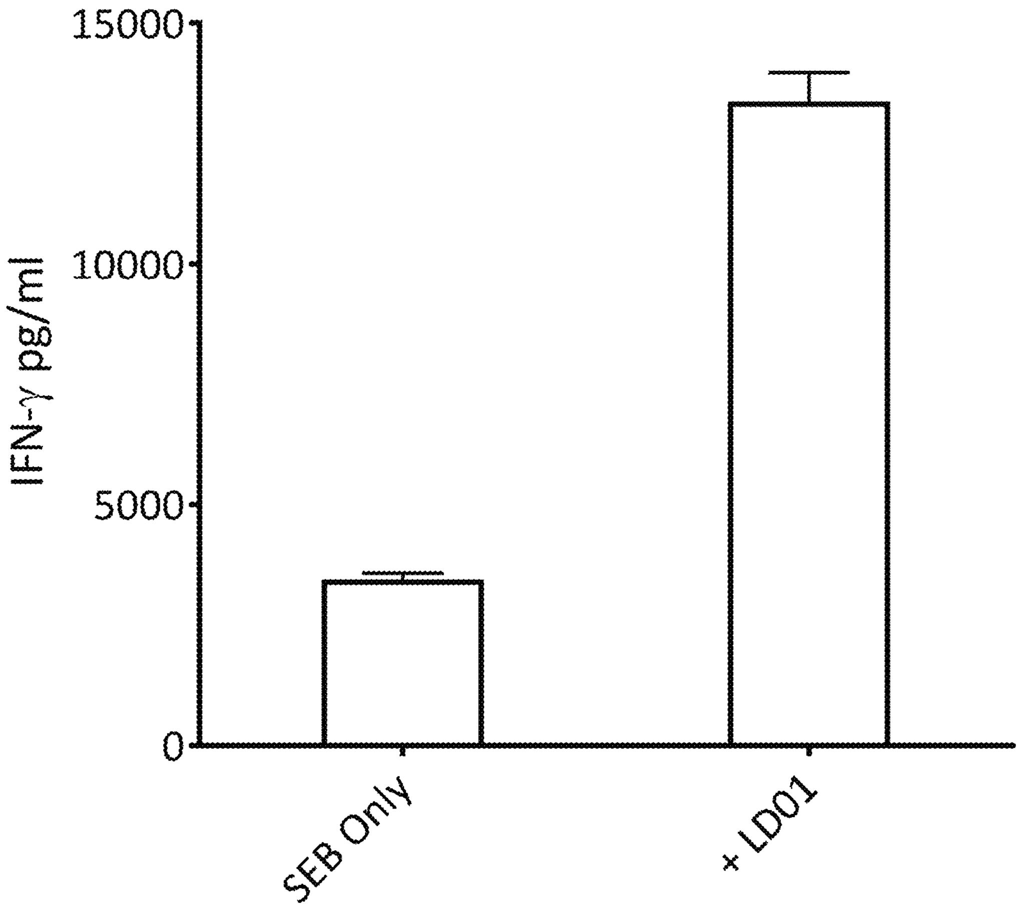
FIG. 15 is a graph showing that peptide LD01 increases IFN-γ secretion by human PBMCs 4-fold relative to Staphylococcal enterotoxin B (SEB) alone.

Human PBMCs from a healthy individual were stimulated with 5 ng/ml of Staphylococcal enterotoxin B (SEB)+/−LD01 (100 μM). At 72 hours, supernatants were collected, and IFN-γ was measured by cytometric bead arrays. The results, shown in FIG. 15, demonstrate that LD01 increases IFN-γ secretion by human PBMCs 4-fold relative to SEB alone.

REFERENCES

Adams et al., "Big opportunities for small molecules in immuno-oncology," Nature Reviews Drug Discovery Advance Online Publication, Jul. 31, 2016, 20 pages Akinc et al., "A combinatorial library of lipid-like materials for delivery of RNAi therapeutics," Nat. Biotechnol. 26, 561-69, 2008

Akinc et al., "Development of lipidoid-siRNA formulations for systemic delivery to the liver," Mol. Ther. 17, 872-79, 2009

Alsaab et al., "PD-1 and PD-L1 Checkpoint Signaling Inhibition for Cancer Immunotherapy: Mechanism, Combinations, and Clinical Outcome," Front. Pharmacol. 8, 561, 2017

Anderson et al., "semi-automated synthesis and screening of a large library of degradable cationic polymers for gene delivery," Angew. Chemi Int. Ed. 42, 3153-58, 2003

Andtbacka et al., "OPTiM: A randomized phase III trial of talimogene laherparepvec (T-VEC) versus subcutaneous (SC) granulocyte-macrophage colony-stimulating factor (GM-CSF) for the treatment (tx) of unresected stage IIIB/C and IV melanoma," J. Clin. Oncol. 31, abstract number LBA9008, 2013

Beavis et al., "Adenosine Receptor 2A Blockade Increases the Efficacy of Anti-PD-1 through Enhanced Antitumor T-cell Responses," Cancer Immunol. Res. 3, 506-17, 2015

Behlke, "Chemical modification of siRNAs for in vivo use," Oligonucleotides. 2008; 18:305-19.

Behr, "The proton sponge: a trick to enter cells the viruses did not exploit," Int. J. Chem. 2, 34-36, 1997

Bensinger et al., "A phase 1 study of lucatumumab, a fully human anti-CD40 antagonist monoclonal antibody administered intravenously to patients with relapsed or refractory multiple myeloma," Br J Haematol. 159, 58-66, 2012.

Benson & Caligiuri, "Killer Immunoglobulin-like Receptors and Tumor Immunity," Cancer Immunol Res 2014; 2:99-104

Bodanszky et al., Peptide Synthesis, John Wiley and Sons, 2d ed. (1976)

Boussif et al., "A versatile vector for gene and oligonucleotide transfer into cells in culture and in vivo: polyethylenimine," Proc. Nat'l. Acad. Sci. (USA) 92, 7297-301, 1995

Bramsen et al., "A large-scale chemical modification screen identifies design rules to generate siRNAs with high activity, high stability and low toxicity," Nucleic Acids Res. 2009; 37:2867-81

Bruno et al., "Basics and recent advances in peptide and protein drug delivery," Ther. Deliv. 4, 1443-67, 2013

Bu et al., "Learning from PD-1 Resistance: New Combination Strategies," Trends Mol. Med. 22, 448-51, 2016

Burnett & Rossi, "RNA-based Therapeutics—Current Progress and Future Prospects," Chem Biol. 19, 60-71, 2012

Cao, "Advances in Delivering Protein and Peptide Therapeutics," Pharmaceutical Technology 40, 22-24, Nov. 2, 2016

Chan & McFadden, "Oncolytic Poxviruses," Ann. Rev. Virol. 1, 119-41, 2014

Chen et al., "Rapid discovery of potent siRNA-containing lipid nanoparticles enabled by controlled microfluidic formulation," J. Am. Chem. Soc. 134, 6948-51, 2012

Cherkassky et al., "Human CAR T cells with cell-intrinsic PD-1 checkpoint blockade resist tumor-mediated inhibition," J. Clin. Invest. 126, 3130-44, 2016

Chiu et al., "siRNA function in RNAi: a chemical modification analysis," RNA 2003; 9:1034-48.

Chong et al., "PD-1 blockade modulates chimeric antigen receptor (CAR)-modified T cells: refueling the CAR," Blood. 129(8), 1039-41, 2017, published on-line Dec. 28, 2016

Chowdhury et al., "Combination therapy strategies for improving PD-1 blockade efficacy: a new era in cancer immunotherapy," J. Int. Med. doi: 10.1111/joim.12708, Epub ahead of print, Oct. 26, 2017
Creative Biolabs User Manual, "TriCo-20TM Phage Display 20-mer Random Peptide Library," 14 pages, Aug. 4, 2009
Dahlman et al., "In vivo endothelial siRNA delivery using polymeric nanoparticles with low molecular weight," Nat. Nanotechnol. 9, 648-55, 2014
Dempke et al., "Second- and third-generation drugs for immuno-oncology treatment—The more the better?" Eur. J. Cancer 74, 55-72, March 2017
Desigaux et al., "Self-assembled lamellar complexes of siRNA with lipidic aminoglycoside derivatives promote efficient siRNA delivery and interference," Proc. Nat'l. Acad. Sci. (USA) 104, 16534-39, 2007
Differding, "AUNP-12—A Novel Peptide Therapeutic Targeting PD-1 Immune Checkpoint Pathway for Cancer Immunotherapy—Structure Activity Relationships & Peptide/Peptidomimetic Analogs," available at differding.com/data/AUNP_12_A_novel_peptide_therapeutic_targeting_PD_1_immune_checkpoint_pathway_ for_cancer_immunotherapy.pdf, Feb. 26, 2014
Dong et al., "Lipopeptide nanoparticles for potent and selective siRNA delivery in rodents and nonhuman primates," Proc. Nat'l. Acad. Sci. (USA) 111, 3955-60, 2014
Dosta et al., "Surface charge tunability as a powerful strategy to control electrostatic interaction for high efficiency silencing, using tailored oligopeptide-modified poly(beta-amino ester)s (PBAEs)," Acta Biomater. 20, 82-93, 2015
Duraiswamy et al., "Dual Blockade of PD-1 and CTLA-4 Combined with Tumor Vaccine Effectively Restores T-Cell Rejection Function in Tumors," Cancer Res 73, 3591-603, 2013
Fenton et al., "Bioinspired alkenyl amino alcohol ionizable lipid materials for highly potent in vivo mRNA delivery," Adv. Mater. 28, 2939-43, 2016
Feridooni et al., "Noninvasive Strategies for Systemic Delivery of Therapeutic Proteins—Prospects and Challenges," Chapter 8 of Sezer, ed., Smart Drug Delivery System, available at http.//www.intechopen.com/books/smart-drug-delivery-system, Feb. 10, 2016
Freeman et al., "Phase I/II trial of intravenous NDV-HUJ oncolytic virus in recurrent glioblastoma multiforme," Mol. Ther. 13, 221-28, 2006
Gao et al., "VISTA is an inhibitory immune checkpoint that is increased after ipilimumab therapy in patients with prostate cancer," Nature Med. 23, 551-55, 2017
Geevarghese et al., "Phase I/II Study of Oncolytic *Herpes Simplex* Virus NV1020 in Patients with Extensively Pretreated Refractory Colorectal Cancer Metastatic to the Liver," Hum. Gene Ther. 21, 1119-28, 2010
Guo et al., "Systemic delivery of therapeutic small interfering RNA using a pH-triggered amphiphilic poly-L-lysinenanocarrier to suppress prostate cancer growth in mice," Eur. J. Pharm. Sci. 45, 521-32, 2012
Harvey et al., "Efficacy of anti-ICOS agonist monoclonal antibodies in preclinical tumor models provides a rationale for clinical development as cancer immunotherapeutics," Journal for ImmunoTherapy of Cancer 3 (Suppl 2), O9, 2015
He et al., "Lymphocyte-activation gene-3, an important immune checkpoint in cancer," Cancer Sci. 107, 1193-97, 2016
Howard et al., "RNA interference in vitro and in vivo using a novel chitosan/siRNA nanoparticle system," Mol. Ther. 14, 476-84, 2006
Huseni et al., "Anti-tumor efficacy and biomarker evaluation of agonistic anti-OX40 antibodies in preclinical models," Journal for ImmunoTherapy of Cancer 2 (Suppl 3), P105, 2014
Infante et al., "A phase Ib dose escalation study of the OX40 agonist MOXR0916 and the PD-L1 inhibitor atezolizumab in patients with advanced solid tumors," J Clin Oncol. 34(suppl; abstr 101), 2016
John et al., "Blockade of PD-1 immunosuppression boosts CAR T-cell therapy," OncoImmunology 2, e26286, 3 pages, 2013
Johnson et al., "A Cancer Research UK phase I study evaluating safety, tolerability, and biological effects of chimeric anti-CD40 monoclonal antibody (MAb), Chi Lob 7/4," J Clin Oncol. 28, 2507, 2010.
Johnson et al., "Clinical and Biological Effects of an Agonist Anti-CD40 Antibody: A Cancer Research UK Phase I Study," Clin Cancer Res 21, 1321-28, 2015
Judge & MacLachlan, "Overcoming the innate immune response to small interfering RNA," Hum Gene Ther. 2008; 19:111-24.
Kaczmarek et al., "Advances in the delivery of RNA therapeutics: from concept to clinical reality," Genome Medicine 2017; 9:60, 16 pages
Kanasty et al., "Delivery materials for siRNA therapeutics," Nat. Mater. 12, 967-77, 2013
Kauffman et al., "Optimization of lipid nanoparticle formulations for mRNA delivery in vivo with fractional factorial and definitive screening designs," Nano Lett. 15, 7300-06, 2015
Kauffman et al., "Efficacy and immunogenicity of unmodified and pseudouridine-modified mRNA delivered systemically with lipid nanoparticles in vivo," Biomaterials. 2016; 109:78-87.
Kaufmann et al., "Chemovirotherapy of Malignant Melanoma with a Targeted and Armed Oncolytic Measles Virus," J. Invest. Dermatol. 133, 1034-42, 2013
Kavikansky & Pavlick, "Beyond Checkpoint Inhibitors: The Next Generation of Immunotherapy in Oncology," Amer. J. Hematol. Oncol. 13, 9-20, 2017
Khubchandani et al., "Dacetuzumab, a humanized mAb against CD40 for the treatment of hematological malignancies," Curr Opin Investig Drugs 10, 579-87, 2009.
Khuri et al., "A controlled trial of intratumoral ONYX-015, a selectively-replicating adenovirus, in combination with cisplatin and 5-fluorouracil in patients with recurrent head and neck cancer," Nat. Med. 6, 879-85, 2000
Kontermann, "Half-life extended biotherapeutics," Expert Opin. Biol. Ther. 16, 903-15, 2016.
Kozielski et al., "A bioreducible linear poly(O-amino ester) for siRNA delivery," Chem. Commun. (Camb). 49, 5319-21, 2013
Lawler et al., "Oncolytic Viruses in Cancer Treatment," JAMA Oncol. 3, 841-49, 2017 (published on-line Jul. 21, 2016)
Le Mercier et al., "VISTA Regulates the Development of Protective Antitumor Immunity," Cancer Res 2014; 74:1933-1944
Leone et al., "A2aR antagonists: Next generation checkpoint blockade for cancer immunotherapy," Computational and Structural Biotechnology Journal 13, 265-72, 2015

Leus et al., "VCAM-1 specific PEGylated SAINT-based lipoplexes deliver siRNA to activated endothelium in vivo but do not attenuate target gene expression," Int. J. Pharm. 469, 121-31, 2014
Li et al., "Discovery of peptide inhibitors targeting human programmed death 1 (PD-1) receptor," Oncotarget 7, 64967-76, Aug. 12, 2016
Li et al., "Effects of chemically modified messenger RNA on protein expression," Bioconjug Chem. 2016; 27:849-53.
Liang, "Oncorine, the World First Oncolytic Virus Medicine and its Update in China," Curr. Cancer Drug Targets 18, 171-76, 2018
Linch et al., "OX40 agonists and combination immunotherapy: putting the pedal to the metal," Frontiers in Oncology 5, 14 pages, 2015
Liu et al., "Immune-checkpoint proteins VISTA and PD-1 nonredundantly regulate murine T-cell responses," Proc. Nat'l. Acad. Sci. USA 112, 6682-87, 2015
Lorence et al., "Phase 1 clinical experience using intravenous administration of PV701, an oncolytic Newcastle disease virus," Curr. Cancer Drug Targets 7, 157-67, 2007
Lorenz et al., "Steroid and lipid conjugates of siRNAs to enhance cellular uptake and gene silencing in liver cells," Bioorganic Med. Chem. Lett. 14, 4975-77, 2004
Love et al., "Lipid-like materials for low-dose, in vivo gene silencing," Proc. Nat'l. Acad. Sci. (USA) 107, 1864-69, 2010
Lu et al., "Replicating retroviral vectors for oncolytic virotherapy of experimental hepatocellular carcinoma," Oncol. Rep. 28, 21-26, 2012
Lundstrom, "Oncolytic Alphaviruses in Cancer Immunotherapy," Vaccines 5, pages 1-17, 2017
Lynn & Langer, "Degradable poly(O-amino esters): synthesis, characterization, and self-assembly with plasmid DNA," J. Am. Chem. Soc. 122, 10761-18, 2000
Magiera-Mularz et al., "Bioactive macrocyclic inhibitors of the PD-1/PD-L1 immune checkpoint," Angewandte Chemie Int. Ed. 10.1002/anie.201707707, e-published Sep. 26, 2017
Maute et al., "Engineering high-affinity PD-1 variants for optimized immunotherapy and immuno-PET imaging," Proc. Natl. Acad. Sci. USA, E6506-E6514, published online Nov. 10, 2015
McDonald et al., "A measles virus vaccine strain derivative as a novel oncolytic agent against breast cancer," Breast Cancer Treat. 99, 177-84, 2006
McOmie, Protective Groups in Organic Chemistry, Plenum Press, New York, N.Y., 1973
Mediavilla-Varela et al., "A Novel Antagonist of the Immune Checkpoint Protein Adenosine A2a Receptor Restores Tumor-Infiltrating Lymphocyte Activity in the Context of the Tumor Microenvironment," Neoplasia 19, 530-36, 2017
Mellemgaard et al., "Combination immunotherapy with IDO vaccine and PD-1 inhibitors in advances HSCLC," DOI: 10.1200/JCO.2017.35.15_suppl.TPS2610 Journal of Clinical Oncology 35, no. 15_suppl—published online before print, 2017
Merrifield, "Solid phase peptide synthesis I: Synthesis of a tetrapeptide," J. Am. Chem. Soc. 85:2149-54, 1963
Messenheimer et al., "Timing of PD-1 Blockade Is Critical to Effective Combination Immunotherapy with Anti-OX40," Clin. Cancer Res. 23, DOI: 10.1158/1078-0432.CCR-16-2677 Published October 2017
Michaelson et al., "Preclinical evaluation of JTX-2011, an anti-ICOS agonist antibody,", Abstract 573, Proceedings: AACR 107th Annual Meeting 2016; Apr. 16-20, 2016; New Orleans, LA
Morrissey et al., "Immunotherapy and Novel Combinations in Oncology: Current Landscape, Challenges, and Opportunities," Clinical and Translational Science 9, 89-104, 2016
Morrissey et al., "Potent and persistent in vivo anti-HBV activity of chemically modified siRNAs," Nat. Biotechnol. 23, 1002-07, 2005
Moschos et al., "Lung delivery studies using siRNA conjugated to TAT(48-60) and penetratin reveal peptide induced reduction in gene expression and induction of innate immunity," Bioconjug. Chem. 18, 1450-59, 2007
Nair et al., "Multivalent N-acetylgalactosamine-conjugated siRNA localizes in hepatocytes and elicits robust RNAi-mediated gene silencing," J. Am. Chem. Soc. 136, 16958-61, 2014
Neurath et al., eds., The Proteins, Vol. II, 3d ed., pp. 105-237, Academic Press, New York, NY (1976)
Nishina et al., "Efficient in vivo delivery of siRNA to the liver by conjugation of alphatocopherol.," Mol. Ther. 16, 734-40, 2008
Ott et al., "Combination immunotherapy: a road map," J. ImmunoTherapy of Cancer 5, 16, 2017
Pack et al., "Design and development of polymers for gene delivery," Nat. Rev. Drug discov. 4, 581-93, 2005
Patel et al., "Recent Advances in Protein and Peptide Drug Delivery: A Special Emphasis on Polymeric Nanoparticles," Protein. Pept. Lett. 21, 1102-20, 2014
Penchala et al., "A biomimetic approach for enhancing the in vivo half-life of peptides," Nat. Chem. Biol. 11, 793-98, 2015
Phuangsab et al., "Newcastle disease virus therapy of human tumor xenografts: antitumor effects of local or systemic administration," Cancer Lett. 172, 27-36, 2001
Prakash et al., "Positional effect of chemical modifications on short interference RNA activity in mammalian cells," J Med Chem. 2005; 48:4247-53
Pratt & MacRae, "The RNA-induced silencing complex: a versatile gene-silencing machine," J Biol Chem. 2009; 284:17897-901
Rehman et al., "Mechanism of polyplex- and lipoplexmediated delivery of nucleic acids: real-time visualization of transient membrane destabilization without endosomal lysis," ACS Nano. 7, 3767-77, 2013
Rivera et al., "Hair Repigmentation During Immunotherapy Treatment With an Anti-Programmed Cell Death 1 and Anti-Programmed Cell Death Ligand 1 Agent for Lung Cancer," JAMA Dermatol. 153, 1162-65, 2017
Rodriguez et al., "Design and implementation of a high yield production system for recombinant expression of peptides," Microbial Cell Factories 13, 65, 10 pages, 2014
Rudin et al., "Phase I clinical study of Seneca Valley Virus (SVV-001), a replication-competent picomavirus, in advanced solid tumors with neuroendocrine features," Clin. Cancer Res. 17, 888-95, 2011
Sahin et al., "mRNA-based therapeutics—developing a new class of drugs," Nat Rev Drug Discov. 2014; 13:759-80
Sakuishi et al., "Targeting Tim-3 and PD-1 pathways to reverse T cell exhaustion and restore anti-tumor immunity," J. Exp. Med. 20, 2187-94, 2010
Schaer et al., "Modulation of GITR for cancer immunotherapy," Curr Opin Immunol. 24, 217-24, 2012
Schroeder et al., "Lipid-based nanotherapeutics for siRNA delivery," J. Int. Med. 267, 9-21, 2010

Sharma & Allison, "Immune Checkpoint Targeting in Cancer Therapy: Toward Combination Strategies with Curative Potential," Cell 161, 205-14, 2015
Shindo et al., "Combination Immunotherapy with 4-1BB Activation and PD-1 Blockade Enhances Antitumor Efficacy in a Mouse Model of Subcutaneous Tumor," Anticancer Res. 35, 129-36, 2015
Shrimali et al., "Concurrent PD-1 Blockade Negates the Effects of OX40 Agonist Antibody in Combination Immunotherapy through Inducing T-cell Apoptosis," Cancer Immunol Res 5(9), pages OF1-12, Aug. 28, 2017
Skalniak et al., "Small-molecule inhibitors of PD-1/PD-L1 immune checkpoint alleviate the PD-L1-induced exhaustion of T-cells," Oncotarget, Advance Publications, Aug. 7, 2017, 15 pages
Smith, "Pigmented skin lesions lightened during melanoma immunotherapy," http://www.mdedge.com/edermatologynews/article/132598/melanoma/pigmented-skin-lesions-lightened-during-melanoma, Mar. 2, 2017
Soutschek et al., "Therapeutic silencing of an endogenous gene by systemic administration of modified siRNAs," Nature. 2004; 432:173-78
Spodzieja et al., "Design of short peptides to block BTLA/HVEM interactions for promoting anticancer T-cell responses," PLoS ONE 12(6): e0179201, 17 pages, 2017
Stojdl et al., "Exploiting tumor-specific defects in the interferon pathway with a previously unknown oncolytic virus," Nat. Med. 6, 821-25, 2000
Stojdl et al., "VSV strains with defects in their ability to shutdown innate immunity are potent systemic anti-cancer agents," Cancer Cell 4, 263-75, 2003 Stuart & Young, Solid Phase Peptide Synthesis, Pierce Chemical Company, Rockford, IL, 1984
Tigue et al., "MEDI1873, a potent, stabilized hexameric agonist of human GITR with regulatory T-cell targeting potential," ONCOIMMUNOLOGY 6(3), e1280645 (14 pages), Feb. 3, 2017
Triebel et al., "LAG-3, a novel lymphocyte activation gene closely related to CD4," J. Exp. Med. 171, 1393-405, 1990
Tsutsumi et al., "Evaluation of polyamidoamine dendrimer/alpha-cyclodextrin conjugate (generation 3, G3) as a novel carrier for small interfering RNA (siRNA)," J. Control. Release 119, 349-59, 2007
Tuck, "Development of Small Molecule Checkpoint Inhibitors," Immune Checkpoint Inhibitors Symposium, 28 pages, Mar. 14-16, 2017
Tzeng et al., "Cystamine-terminated poly(beta-amino ester)s for siRNA delivery to human mesenchymal stem cells and enhancement of osteogenic differentiation," Biomaterials 33, 8142-51, 2012
Tzeng et al., "PD-1 blockage reverses immune dysfunction and hepatitis B viral persistence in a mouse animal model," PLoS One 7(6):e39179, 2012
Van Dessel et al., "Potent and tumor specific: arming bacteria with therapeutic proteins," Ther. Deliv. 6, 385-99, 2015
Vonderheide and Glennie, "Agonistic CD40 antibodies and cancer therapy," Clin. Cancer Res. 19, 1035-43, 2013
Vonderheide et al., "Clinical activity and immune modulation in cancer patients treated with CP-870,893, a novel CD40 agonist monoclonal antibody," J Clin Oncol. 25, 876-83, 2007
Wang et al., "Anaplastic lymphoma kinase (ALK) inhibitors: a review of design and discovery," Med. Chem. Commun. 5, 1266-79, 2014
Wang et al., "VISTA, a novel mouse Ig superfamily ligand that negatively regulates T cell responses," J. Exp. Med. 208, 577-92, 2011
Wittrup & Lieberman, "Knocking down disease: a progress report on siRNA therapeutics," Nat Rev Genet. 2015; 16:543-52
Won et al., "Missing pieces in understanding the intracellular trafficking of polycation/DNA complexes," J. Control. Release 139, 88-93, 2009
Xia et al., "Antibody-mediated targeting of siRNA via the human insulin receptor using avidin—biotin technology.," Mol. Pharm. 6, 747-51, 2009
Yang et al., "Oral vaccination with *salmonella* simultaneously expressing *Yersinia pestis* F1 and V antigens protects against bubonic and pneumonic plague," J Immunol. 178, 1059-67, 2007
Ye et al., "T-cell exhaustion in chronic hepatitis B infection: current knowledge and clinical significance," Cell Death Dis. 19, e1694, 2015
Young et al., "Co-inhibition of CD73 and A2AR Adenosine Signaling Improves Anti-tumor Immune Responses," Cancer Cell 30, 391-403, 2016
Yu et al., "Disposition and pharmacology of a GalNAc3-conjugated ASO targeting human lipoprotein(a) in mice," Mol. Ther. Nucleic Acids 5, e317, 2016
Zarganes-Tzitzikas et al., "Inhibitors of programmed cell death 1 (PD-1): a patent review," Expert Opinion on Therapeutic Patents 26, 973-77, published on-line Jul. 6, 2016
Zhan et al., "From monoclonal antibodies to small molecules: the development of inhibitors targeting the PD-1/PD-L1 pathway," Drug Discovery Today 21, 1027-36, June 2016
Zorzi et al., "Acylated heptapeptide binds albumin with high affinity and application as tag furnishes long-acting peptides," Nature Communications 8, 16092, 2017

The invention claimed is:

1. A pharmaceutical composition comprising an RNA encoding a peptide, wherein the RNA comprises a modification selected from the group consisting of (i) modification of a ribose sugar, (ii) modification of a phosphate linkage, and (iii) modification of a base, and wherein the peptide is selected from the group consisting of:

(1) LD01 (SEQ ID NO:1), LD11 (SEQ ID NO:5), LD10 (SEQ ID NO:12), LD10 R9A (SEQ ID NO:15), LD10 P15A (SEQ ID NO:17), LD17 (SEQ ID NO:21), LD17m (SEQ ID NO:22), LD10da (SEQ ID NO:24), LD01 TQ19 aa (SEQ ID NO:29), LD01 TQ19 da (SEQ ID NO:30), peptide LD01(u) (SEQ ID NO:36), peptide LD17m(u) (SEQ ID NO:37), and peptide LD01 TQ19 (u) (SEQ ID NO:38);

(2) selected from the group consisting of LD01 (SEQ ID NO:1), LD11 (SEQ ID NO:5), LD10 (SEQ ID NO:12), LD10 R9A (SEQ ID NO:15), LD10 P15A (SEQ ID NO:17), LD17 (SEQ ID NO:21), LD17m (SEQ ID NO:22), LD10da (SEQ ID NO:24), LD01 TQ19 aa (SEQ ID NO:29), and LD01 TQ19 da (SEQ ID NO:30), and peptide a (SEQ ID NO:36), peptide LD17m(u) (SEQ ID NO:37), and peptide LD01 TQ19(u) (SEQ ID NO:38), wherein the peptide comprises one or more modifications selected from the group consisting of C-terminal amidation, N-terminal acetylation, and replacement of at least and one L-amino acid with a corresponding D-amino acid; and (3) selected from the group consisting of LD01 (SEQ ID NO:1), LD11 (SEQ ID NO:5), LD10 (SEQ ID NO:12), LD10 R9A (SEQ ID NO:15), LD10 P15A (SEQ ID NO:17), LD17 (SEQ ID NO:21), LD17m (SEQ ID NO:22), LD01 TQ19 aa (SEQ ID NO:29), and LD01r (SEQ ID NO:11), peptide LD01(u) (SEQ ID NO:36), peptide LD17m(u) (SEQ ID NO:37), and peptide LD01 TQ19(u) (SEQ ID NO:38), wherein the N-terminal amino acid is a D amino acid.

2. The pharmaceutical composition of claim 1, wherein the modification is selected from the group consisting of a ribo-difluorotoluyl nucleotide, a 4'-thio modified RNA, a boranophosphate linkage, a phosphorothioate linkage, a 2'-O-methyl (2'-OMe) sugar substitution, a 2'-fluoro (2'-F), a 2'-O-methoxyethyl (2'-MOE) sugar substitution, a locked nucleic acid (LNA), and an L-RNA.

3. The pharmaceutical composition of claim 1 wherein the peptide is LD01 (SEQ ID NO:1).

4. The pharmaceutical composition of claim 1, wherein the peptide is LD10 (SEQ ID NO:12).

5. The pharmaceutical composition of claim 1, wherein the peptide is selected from the group consisting of LD01 (SEQ ID NO:1), LD11 (SEQ ID NO:5), LD10 (SEQ ID NO: 12), LD10 R9A (SEQ ID NO:15), LD10 P15A (SEQ ID NO:17), LD17 (SEQ ID NO:21), LD17m (SEQ ID NO:22), LD10da (SEQ ID NO:24), LD01 TQ19 aa (SEQ ID NO:29), LD01TQ19 da (SEQ ID NO:30), peptide LD01(u) (SEQ ID NO:36), peptide LD17m(u) (SEQ ID NO: 37), and peptide LD01 TQ19(u) (SEQ ID NO:38).

6. The pharmaceutical composition of claim 5, wherein the peptide is LD01 (SEQ ID NO:1).

7. The pharmaceutical composition of claim 5, wherein the peptide is LD10 (SEQ ID NO:12).

8. The pharmaceutical composition of claim 1, wherein the peptide is selected from the group consisting of LD01 (SEQ ID NO:1), LD11 (SEQ ID NO:5), LD10 (SEQ ID NO: 12), LD10 R9A (SEQ ID NO:15), LD10 P15A (SEQ ID NO:17), LD17 (SEQ ID NO:21), LD17m (SEQ ID NO:22), LD10da (SEQ ID NO:24), LD01 TQ19 aa (SEQ ID NO:29), and LD01 TQ19 da (SEQ ID NO:30), peptide a (SEQ ID NO:36), peptide LD17m(u) (SEQ ID NO: 37), and peptide LD01 TQ19(u) (SEQ ID NO:38), wherein the peptide comprises one or more modifications selected from the group consisting of C-terminal amidation, N-terminal acetylation, and replacement of at least one L-amino acid with a corresponding D-amino acid.

9. The pharmaceutical composition of claim 8, wherein the peptide is LD01 (SEQ ID NO:1).

10. The pharmaceutical composition of claim 8, wherein the peptide is LD10 (SEQ ID NO:12).

11. The pharmaceutical composition of claim 1, wherein the peptide is selected from the group consisting of LD01 (SEQ ID NO:1), LD11 (SEQ ID NO:5), LD10 (SEQ ID NO: 12), LD10 R9A (SEQ ID NO:15), LD10 P15A (SEQ ID NO:17), LD17 (SEQ ID NO:21), LD17m (SEQ ID NO:22), LD01 TQ19 aa (SEQ ID NO:29), peptide LD01 (u) (SEQ ID NO:36), peptide LD17m(u) (SEQ ID NO:37), and peptide LD01 TQ19(u) (SEQ ID NO:38), wherein the N-terminal amino acid is a D amino acid.

12. The pharmaceutical composition of claim 11, wherein the peptide is LD01 (SEQ ID NO:1).

13. The pharmaceutical composition of claim 11, wherein the peptide is LD10 (SEQ ID NO:12).

* * * * *